United States Patent
Imgrund et al.

(10) Patent No.: US 8,029,277 B2
(45) Date of Patent: Oct. 4, 2011

(54) METHOD AND SYSTEM FOR MEASURING TOOTH DISPLACEMENTS ON A VIRTUAL THREE-DIMENSIONAL MODEL

(75) Inventors: Hans Imgrund, Berlin (DE); Peer Sporbert, Berlin (DE)

(73) Assignee: Orametrix, Inc., Richardson, TX (US)

( * ) Notice: Subject to any disclaimer, the term of this patent is extended or adjusted under 35 U.S.C. 154(b) by 523 days.

(21) Appl. No.: 11/234,591

(22) Filed: Sep. 23, 2005

(65) Prior Publication Data

US 2006/0263741 A1    Nov. 23, 2006

Related U.S. Application Data

(63) Continuation-in-part of application No. 11/133,996, filed on May 20, 2005.

(51) Int. Cl.
*A61C 3/00*    (2006.01)
(52) U.S. Cl. .......................................................... 433/24
(58) Field of Classification Search ................... 433/24, 433/196
See application file for complete search history.

(56) References Cited

U.S. PATENT DOCUMENTS

| | | | |
|---|---|---|---|
| 6,582,227 B2 * | 6/2003 | Phan et al. | 433/24 |
| 2003/0163291 A1 * | 8/2003 | Jordan et al. | 703/1 |

* cited by examiner

*Primary Examiner* — Cris L Rodriguez
*Assistant Examiner* — Heidi M Eide
(74) *Attorney, Agent, or Firm* — Jasvantrai C. Shah

(57) ABSTRACT

It is a common practice with orthodontists in planning treatment for a patient to prescribe dental changes to cure the malocclusion condition of the patient in terms of mesial or distal, buccal or lingual, and occlusal (coronal) or gingival translational displacements; and facial or lingual torque; mesial or distal angulation and mesial or distal rotation displacements. A method and workstation for measuring the dental displacements, or conversely placing the dental elements in desired positions as per the prescriptions for their displacements in a consistent, reproducible and accurate manner is disclosed. A novel orthogonal curvilinear coordinate system is disclosed that enables the measurement of the tooth displacements in conjunction with the individual tooth axes system.

13 Claims, 10 Drawing Sheets

METHOD AND SYSTEM FOR MEASURING TOOTH DISPLACEMENTS ON A VIRTUAL THREE-DIMENSIONAL MODEL

CROSS-REFERENCE TO RELATED APPLICATIONS

This is a continuation-in-part of application entitled "METHOD AND SYSTEM FOR COMPREHENSIVE EVALUATION OF ORTHODONTIC CARE USING UNIFIED WORKSTATION," Ser. No. 11/133,996, filed May 20, 2005, pending, the entire contents of which are incorporated by reference herein.

BACKGROUND OF THE INVENTION

A. Field of the Invention

This invention relates to the field of computerized techniques for orthodontic treatment planning for human patients. More particularly, the invention is directed to measuring tooth displacements in a consistent and accurate manner during virtual orthodontic treatment planning using a novel orthodontic reference coordinate system in conjunction with a tooth axes system. The invention is also directed to moving the teeth from initial positions to desired positions in an accurate, consistent and reproducible manner.

B. Description of Related Art

The traditional process of diagnosis and treatment planning for a patient with orthodontic problems or disease typically consists of the practitioner obtaining clinical history, medical history, dental history, and orthodontic history of the patient supplemented by 2D photographs, 2D radiographic images, CT scans, 2D and 3D scanned images, ultrasonic scanned images, and in general non-invasive and sometimes invasive images, plus video, audio, and a variety of communication records. Additionally, physical models, such as made from plaster of paris, of the patient's teeth are created from the impressions taken of the patient's upper and lower jaws. Such models are manually converted into teeth drawings by projecting teeth on drawing paper. Thus, there is a large volume of images and data involved in the diagnosis and treatment planning process. Furthermore, the information may require conversion from one form to another and selective reduction before it could become useful. There are some computerized tools available to aid the practitioner in these data conversion and reduction steps, for example to convert cephalometric x-rays (i.e., 2 dimensional x-ray photographs showing a lateral view of the head and jaws, including teeth) into points of interest with respect to soft tissue, hard tissue, etc., but they are limited in their functionalities and scope. Even then, there is a fairly substantial amount of manual work involved in these steps.

Orthodontists routinely prescribe translational displacements and rotational movements of teeth of orthodontic patients during treatment planning. The translational displacements include mesial or distal (miseodistal), buccal or lingual (buccolingual), and coronal or gingival displacements. The rotational movements include torque, angulation and rotation. Generally, the translation displacements are specified in mm; and the torque, angulation and rotation movements in gradient or degrees. Additionally, measurements of tooth positions in terms of these translational displacements and rotational movements are used in assessing the treatment needs. Often, a physical model of the dentition of a patient is created and used by the practitioner in manually measuring the tooth positions and assessing the required teeth displacements and movements. The measurements are basically done in two-dimensions and are time consuming, prone to inherent inaccuracies; and lack consistency and reproducibility.

Consequently, the practitioner is left to mental visualization, and chance process to select the treatment course that would supposedly work. Furthermore, the diagnosis process is some-what ad-hoc and the effectiveness of the treatment depends heavily upon the practitioner's level of experience. Often, due to the complexities of the detailed steps and the time consuming nature of them, some practitioners take a shortcut, relying predominantly on their intuition to select a treatment plan. For example, the diagnosis and treatment planning is often done by the practitioner on a sheet of acetate placed over the X-rays. All of these factors frequently contribute towards trial and error, hit-and-miss, lengthy and inefficient treatment plans that require numerous mid-course adjustments. While at the beginning of treatment things generally run well as all teeth start to move at least into the right direction, at the end of treatment a lot of time is lost by adaptations and corrections required due to the fact that the end result has not been properly planned at any point of time. By and large, this approach lacks reliability, reproducibility and precision. More over, there is no comprehensive way available to a practitioner to stage and simulate the treatment process in advance of the actual implementation to avoid the often hidden pitfalls. And the patient has no choice and does not know that treatment time could be significantly reduced if proper planning was done.

In recent years, computer-based approaches have been proposed for aiding orthodontists in their practice. However, these approaches are limited to diagnosis and treatment planning of craniofacial structures, including the straightening of teeth. See Andreiko, U.S. Pat. No. 6,015,289; Snow, U.S. Pat. No. 6,068,482; Kopelmann et al., U.S. Pat. No. 6,099,314; Doyle, et al., U.S. Pat. No. 5,879,158; Wu et al., U.S. Pat. No. 5,338,198, and Chisti et al., U.S. Pat. Nos. 5,975,893 and 6,227,850, the contents of each of which is incorporated by reference herein. Also see imaging and diagnostic software and other related products marketed by Dolphin Imaging, 6641 Independence Avenue, Canoga Park, Calif. 91303-2944.

A method for generation of a 3D model of the dentition from an in-vivo scan of the patient, and interactive computer-based treatment planning for orthodontic patients, is described in U. U.S. Pat. No. 6,648,640 to Rubbert, et al., the contents of which are incorporated by reference herein.

Other background references related to capturing three dimensional models of dentition and associated craniofacial structures include S. M. Yamany and A. A. Farag, "A System for Human Jaw Modeling Using Intra-Oral Images" in *Proc. IEEE Eng. Med. Biol. Soc. (EMBS) Conf*, Vol. 20, Hong Kong, October 1998, pp. 563-566; and M. Yamany, A. A. Farag, David Tasman, A. G. Farman, "A 3-D Reconstruction System for the Human Jaw Using a Sequence of Optical Images," *IEEE Transactions on Medical Imaging*, Vol. 19, No. 5, May 2000, pp. 538-547. The contents of these references are incorporated by reference herein.

The technical literature further includes a body of literature describing the creation of 3D models of faces from photographs, and computerized facial animation and morphable modeling of faces. See, e.g., Pighin et al., *Synthesizing Realistic Facial Expression from Photographs*, Computer Graphics Proceedings SIGGRAPH '98, pp. 78-94 (1998); Pighin et al., *Realistic Facial Animation Using Image-based 3D Morphing*, Technical Report no. UW-CSE-97-01-03, University of Washington (May 9, 1997); and Blantz et al., *A Morphable Model for The Synthesis of 3D Faces*, Computer Graphics Proceedings SIGGRAPH '99 (August, 1999). The contents of these references are incorporated by reference herein.

The computerized treatment planning has created a vital need for realizing desired tooth displacements and movements, and making tooth position measurements in a consistent, accurate and reproducible manner during virtual orthodontic treatment planning.

Therefore, a novel method and system are disclosed for realizing the desired tooth displacements and rotational movements; and measuring tooth positions in a consistent, accurate and reproducible manner. This is enabled by a novel orthodontic reference coordinate system for calculating tooth displacements and movements in a meaningful manner that obviates the shortcomings of the traditional approach discussed above.

SUMMARY OF THE INVENTION

In a first aspect of the invention, a novel orthodontic reference coordinate system, herein referred to as the Orthogonal Curvilinear Coordinate System (OCCS), is disclosed that, in conjunction with individual tooth axis system (TAS), enables accurate, consistent and reproducible measurements of the tooth translation displacements, such as mesiodistal displacement, buccolingual displacement and coronal (buccal)-gingival displacement; and rotational movements, such as torque, angulation and rotation; and positioning of virtual teeth at desired positions. The TAS is created for each individual tooth based up on the ideal properties of the tooth in terms of its features. TAS is preferably an anatomical coordinate system for the tooth. It is preferably derived during virtual modelling of the tooth from the scanning data and the tooth templates. TAS comprises an origin, the x-axis in the mesial and distal directions, the y-axis in the buccal and lingual directions and the z-axis in the occlusal and gingival (vertical) directions. Then, the OCCS, based on the virtual arch (VA) jaw feature is created for each jaw as follows: First an arbitrary plane containing a monotonously curved virtual arch (VA) is identified such that (a) preferably the sum of the squares of the orthogonal distances, of the TAS origins for all the teeth in the jaw, from the plane is the minimum; and (b) the sum of the squares of the orthogonal distances, of the orthogonal projection points on the plane corresponding to the TAS origins, from the VA is also the minimum. Alternately, the sum of the TAS origin orthogonal distances from the plane is minimized; and also the sum of the TAS origin projection point orthogonal distances from the VA is minimized. Through the two orthogonal projections, first from the TAS origin to the plane, and then from the TAS origin orthogonal projection point to the VA, a point on the VA is identified as the origin of the OCCS for each tooth. Then, the OCCS coordinate axes are computed such that the x-axis coincides with the tangent to the VA at the OCCS origin for the tooth; the y-axis coincides with the normal to the x-axis at the OCCS origin for the tooth; and the z axis as orthogonal to the plane formed by the x-axis and the y-axis, and located at the OCCS origin for the tooth.

In another aspect of the invention, a method for measuring the mesiodistal displacement of a tooth in a given position using the OCCS and the TAS is disclosed. The mesiodistal displacement for the tooth is the length of the bow segment along the VA between the OCCS origin and the position of the tooth. The procedure can be repeated for the tooth in an initial position and then in a target position to calculate the mesiodistal displacement in each case, and the difference between the two displacement measurements is the relative displacement between the two positions of the tooth. A similar procedure can be used to position a tooth at a desired mesiodistal displacement with respect to the tooth's OCCS origin. Similarly, a tooth can be moved from its initial position to a target positon at a desired mesiodistal displacement from the initial position using the OCCS.

In another aspect of the invention, a method for measuring the buccolingual displacement of a tooth in a given position using the OCCS and the TAS is disclosed. The buccolingual displacement for a tooth is the orthogonal distance between the plane which contains the z-axis of the OCCS (z-axis plane) and the plane which contains the origin of the TAS for the tooth and is parallel to the z-axis plane. The procedure can be repeated for the tooth in an initial position and then in a target position to calculate the buccolingual displacement in each case; and the appropriate sum of or the difference between the two displacement measurements would be the relative displacement between the two positions of the tooth. A similar procedure can be used to position a tooth at a desired buccolingual displacement with respect to the tooth's OCCS. Similarly, a tooth can be moved from its initial position to a target position at a desired buccolingual displacement from the initial position using the OCCS.

In another aspect of the invention, a method for measuring the coronal-gingival displacement of a tooth in a given position using the OCCS and the TAS is disclosed. The coronal-gingival displacement for the tooth is the orthogonal distance between the plane which contains the y-axis of the OCCS (y-axis plane) and the plane which contains the origin of the TAS for the tooth and is parallel to the y-axis plane. The procedure can be repeated for the tooth in an initial position and then in a target position to calculate the coronal-gingival displacement in each case; and the appropriate sum of or the difference between the two displacement measurements would be the relative displacement between the two positions of the tooth. A similar procedure can be used to position a tooth at a desired coronal-gingival displacement with respect to the tooth's OCCS. Similarly, a tooth can be moved from its initial position to a target position at a desired coronal-gingival displacement from the initial position using the OCCS.

In another aspect of the invention, a method for measuring the torque for a tooth in a given position using the OCCS and the TAS is disclosed. The torque for a tooth is measured in degrees as the angle $\alpha$ between the z-axis of the TAS for the tooth and the line which passes through the origin of the TAS and is drawn parallel to the z-axis of the OCCS, when viewed from the perspective of the x-axis direction of the OCCS. The procedure can be repeated for the tooth in an initial position and then in a target position to calculate the torque in each case; and the appropriate sum of, or the difference between, the two torque measurements would be the relative torque between the two positions of the tooth. A similar procedure can be used to position a tooth at a desired torque with respect to the tooth's OCCS. Similarly, a tooth can be moved from its initial position to a target position having the desired torque with respect to the initial position using the OCCS and TAS.

In another aspect of the invention, a method for measuring the angulation for a tooth in a given position using the OCCS and the TAS is disclosed. The angulation for the tooth is measured in degrees as the angle $\beta$ between the z-axis of the TAS for the tooth and the line which passes through the origin of the TAS and is drawn parallel to the z-axis of the OCCS, when viewed from the perspective of the y-axis direction of the OCCS. The procedure can be repeated for the tooth in an initial position and then in a target position to calculate the angulation in each case; and the appropriate sum of, or the difference between, the two angulation measurements would be the relative angulation between the two positions of the tooth. A similar procedure can be used to position a tooth at a desired angulation with respect to the tooth's OCCS. Similarly, a tooth can be moved from its initial position to a target position having the desired angulation with respect to the initial position using the OCCS and TAS.

In another aspect of the invention, a method for measuring the rotation for a tooth in a given position using the OCCS and the TAS is disclosed. The rotation for the tooth, once the TAS has been transformed such that the z-axis of the TAS is parallel to the z-axis of the OCCS, is measured in degrees as the angle θ between the y-axis of the OCCS and the y-axis of the TAS, when viewed from the perspective of the z-axis direction of the OCCS. The procedure can be repeated for the tooth in an initial position and then in a target position to calculate the rotation in each case; and the appropriate sum of, or the difference between, the two rotation measurements would be the relative rotation between the two positions of the tooth. A similar procedure can be used to position a tooth at a desired rotation with respect to the tooth's OCCS, once the tooth TAS has been transformed as described above. Similarly, a tooth can be moved from its initial position to a target position having the desired rotation with respect to the initial position using the OCCS and transformed TAS.

In yet another aspect of the invention, a workstation comprising a computing platform, memory and other storage devices is disclosed that enables, using OCCS and TAS, the accurate, consistent and reproducible measurements of the tooth translation displacements, such as mesiodistal displacement, buccolingual displacement and coronal (buccal)-gingival displacement; and rotational movements, such as torque, angulation and rotation; and positioning of virtual teeth at desired positions using virtual dentition of a patient.

BRIEF DESCRIPTION OF THE DRAWINGS

Presently preferred embodiments of the invention are described below in reference to the appended drawings, wherein like reference numerals refer to like elements in the various views, and in which:

FIG. 3D also illustrates the axes of the OCCS as a part of the third step in determining the OCCS, according to a preferred embodiment of the invention.

DETAILED DESCRIPTION OF PREFERRED EMBODIMENTS

Before describing the method of realizing consistent tooth displacements and tooth position measurements in virtual orthodontic treatment planning using a novel orthodontic reference coordinate system in conjunction with a tooth axes system of this invention in detail, an overview of a unified workstation will be set forth initially. The workstation provides software features that create two dimensional and/or three-dimensional virtual patient models on a computer, which can be used for the purposes of treatment planning, evaluation and quality measurement.

Many of the details and computer user interface tools which a practitioner may use in adjusting tooth position, designing appliance shape and location, managing space between teeth, and arriving at a finish tooth position using interaction with a computer storing and displaying a virtual model of teeth are set forth in the prior application Ser. No. 09/834,412 filed Apr. 13, 2001, now issued as U.S. Pat. No. 6,632,089, and in U. U.S. Pat. No. 6,648,640 to Rubbert, et al., the contents of each of which are incorporated by reference herein.

General Description

A unified workstation environment and computer system for diagnosis, treatment planning and evaluation and quality measurement, and delivery of therapeutics, especially adapted for treatment of craniofacial structures, is described below.

Figure 1:
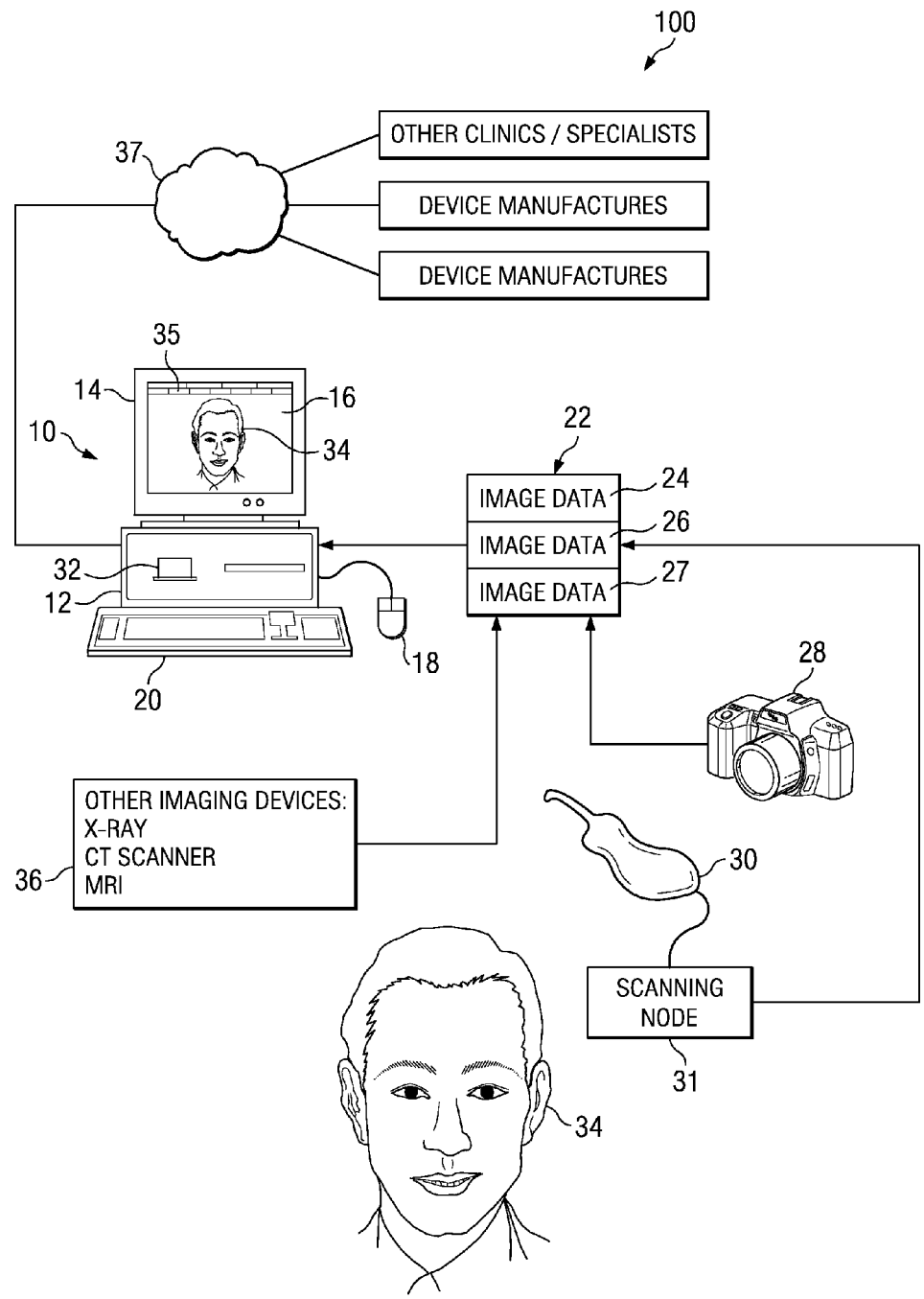
FIG. 1 is block diagram of a system for creating a three-dimensional virtual patient model and for diagnosis and planning treatment of the patient.

The treatment planning system is depicted in FIG. 1. The overall system 100 includes a general-purpose computer system 10 having a processor (CPU 12) and a user interface 14, including screen display 16, mouse 18 and keyboard 20. The system is useful for planning and evaluating treatment for a patient 34.

The system 100 includes a computer storage medium or memory 22 accessible to the general-purpose computer system 10. The memory 22, such as a hard disk memory or attached peripheral devices, stores two or more sets of digital data representing patient craniofacial image information. These sets include at least a first set of digital data 24 representing patient craniofacial image information obtained from a first imaging device and a second set of digital data 26 representing patient craniofacial image information obtained from a second image device different from the first image device. The first and second sets of data represent, at least in part, common craniofacial anatomical structures of the patient. At least one of the first and second sets of digital data normally would include data representing the external visual appearance or surface configuration of the face of the patient.

In a representative and non-limiting example of the data sets, the first data set 24 could be a set of two dimensional color photographs of the face and head of the patient obtained via a color digital camera 28, and the second data set is three-dimensional image information of the patient's teeth, acquired via a suitable scanner 30, such as a hand-held optical 3D scanner, or other type of scanner. The memory 22 may also store other sets 27 of digital image data, including digitized X-rays, MRI or ultrasound images, CT scanner etc., from other imaging devices 36. The other imaging devices need not be located at the location or site of the workstation system 100. Rather, the imaging of the patient 34 with one or other imaging devices 36 could be performed in a remotely located clinic or hospital, in which case the image data is obtained by the workstation 100 over the Internet 37 or some other communications medium, and stored in the memory 22.

The system 100 further includes a set of computer instructions and reference databases or digital libraries stored on a machine-readable storage medium. The instructions and reference databases may be stored in the memory 22 accessible to the general-purpose computer system 10. The machine-readable medium storing the instructions and reference databases may alternatively be a hard disk memory 32 for the computer system 10, external memory devices, or may be resident on a file server on a network connected to the computer system, the details of which are not important. The set of instructions and reference databases, described in more detail below, comprise instructions and reference databases for causing the general computer system 10 to perform several functions related to the generation and use of the virtual patient model in diagnostics, therapeutics and treatment planning, evaluation and quality measurement.

These functions include a function of automatically, and/or with the aid of operator interaction via the user interface 14, superimposing the first set 24 of digital data and the second set 26 of digital data so as to provide a composite, combined digital representation of the craniofacial anatomical structures in a common coordinate system. This composite, combined digital representation is referred to herein occasionally as the "virtual patient model," shown on the display 16 of FIG. 1 as a digital model of the patient 34. Preferably, one of the sets 24, 26 of data includes photographic image data of the patient's face, teeth and head, obtained with the color digital camera 28. The other set of data includes intra-oral 3D scan data obtained from the hand-held scanner 30, CT scan data, X-Ray data, MRI, etc. In the example of FIG. 1, the hand-held scanner 30 acquires a series of images containing 3D information and this information is used to generate a 3D model in the scanning node 31, in accordance with the teachings of the patent application of Rüdger Rubbert et al., filed Apr. 13, 2001, entitled INTERACTIVE AND ARCHWIRE-BASED ORTHODONTIC CARE SYSTEM BASED ON INTRAORAL SCANNING OF TEETH, Ser. No. 09/835,039, now issued as U.S. Pat. No. 6,648,640, the entire contents of which are incorporated by reference herein. Additional data sets are possible, and may be preferred in most embodiments.

The software instructions further includes a set of functions or routines that cause the user interface 16 to display the composite, combined digital three-dimensional representation of craniofacial anatomical structures to a user of the system. In a representative embodiment, computer-aided design (CAD)-type software tools are used to display the model to the user and provide the user with tools for viewing and studying the model. Preferably, the model is capable of being viewed in any orientation. Tools are provided for showing slices or sections through the model at arbitrary, user defined planes. Alternatively, the composite digital representation may be printed out on a printer or otherwise provided to the user in a visual form.

The software instructions further include instructions that, when executed, provide the user with tools on the user interface 14 for visually studying, on the user interface, the interaction of the craniofacial anatomical structures and their relationship to the external, visual appearance of the patient. For example, the tools include tools for simulating changes in the anatomical position or shape of the craniofacial anatomical structures, e.g., teeth, jaw, bone or soft tissue structure, and their effect on the external, visual appearance of the patient. The preferred aspects of the software tools include tools for manipulating various parameters such as the age of the patient; the position, orientation, color and texture of the teeth; reflectivity and ambient conditions of light and its effect on visual appearance. The elements of the craniofacial and dental complex can be analyzed quickly in either static format (i.e., no movement of the anatomical structures relative to each other) or in a dynamic format (i.e., during movement of anatomical structures relative to each other, such as chewing, occlusion, growth, etc.). To facilitate such modeling and simulations, teeth may be modeled as independent, individually moveable three dimensional virtual objects, using the techniques described in the above-referenced U.S. Pat. No. 6,648,640.

The workstation environment provided by this invention provides a powerful system and for purposes of diagnosis, treatment planning and evaluation and quality measurement, and delivery of therapeutics. For example, the effect of jaw and skull movement on the patient's face and smile can be studied. Similarly, the model can be manipulated to arrive at the patient's desired feature and smile. From this model, and more particularly, from the location and position of individual anatomical structures (e.g., individual tooth positions and orientation, shape of arch and position of upper and lower arches relative to each other), it is possible to automatically back solve for or derive the jaw, tooth, bone and/or soft tissue corrections that must be applied to the patient's initial position, which might be pre-treatment position or position at any other time during treatment, to provide the desired result. This leads directly to a patient treatment plan.

These simulation tools comprise user-friendly and intuitive icons 35 that are activated by a mouse or keyboard on the user interface of the computer system 10. When these icons are activated, the software instruction provide pop-up, menu, or other types screens that enable a user to navigate through particular tasks to highlight and select individual anatomical features, change their positions relative to other structures, and simulate movement of the jaws (chewing or occlusion). Examples of the types of navigational tools, icons and treatment planning tools for a computer user interface that may be useful in this process and provide a point of departure for further types of displays are described in the previously referenced patent application of Rudger Rubbert et al., Ser. No. 09/835,039 filed Apr. 13, 2001, now issued as U.S. Pat. No. 6,648,640, the contents of which are incorporated by reference herein.

The virtual patient model, or some portion thereof, such as data describing a three-dimensional model of the teeth in initial and target or treatment positions, is useful information for generating customized orthodontic appliances for treatment of the patient. The position of the teeth in the initial and desired positions can be used to generate a set of customized brackets, and customized flat planar archwire, and customized bracket placement jigs, as described in the above-referenced Andreiko et al. patents.

With the above general description in mind, additional details of the software modules will be described next.

Capture of Image Information

Figure 2:
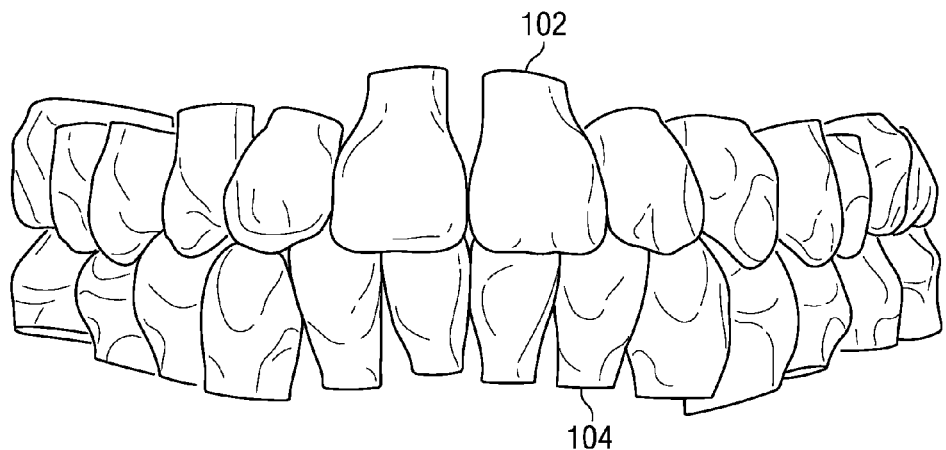
FIG. 2 shows a virtual three-dimensional dentition model of the upper and lower jaws of a patient.

The image data regarding the patient's dentition can be obtained through a variety of means including via scanning of the dentition of the patient via the hand-held 3D-scanner 30 described in the patent application of Rudger Rubbert et al., Ser. No. 09/835,039 filed Apr. 13, 2001, now issued as U.S. Pat. No. 6,648,640, referenced previously. In operation, the scanner captures a sequence of overlapping images of the dentition of the patient as the scanner is held by the hand and moved about the oral cavity. Each image is converted to a set of X, Y and Z coordinate positions comprising a cloud of points representing the surface of the dentition. The point clouds from each image are registered to each other to find a best fit to the data. The resulting registered point cloud is then stored in the memory as a virtual three-dimensional object. The construction, calibration and operation of the scanner, and the manner of converting scanned data to point clouds and registering three-dimensional point clouds to form a three-dimensional object is described at length in the U.S. Pat. No. 6,648,640, referenced earlier and therefore omitted from the present discussion for the sake of brevity. Other types of scanners or coordinate measuring instruments could also be used. FIG. 2 shows a screen shot of a virtual three-dimensional dentition model of the upper jaw 102 and the lower jaw 104 of a patient.

Treatment Planning

The computer or workstation 10 (FIG. 1) that includes the software for generating the patient model preferably includes interactive treatment planning software that allows the user to simulate various possible treatments for the patient on the workstation and visualize the results of proposed treatments on the user interface by seeing their effect on the visual appearance of the patient, especially their smile. The interactive treatment planning preferably provides suitable tools and icons that allow the user to vary parameters affecting the patient. Such parameters would include parameters that can be changed so as to simulate change in the age of the patient, and parameters that allow the user to adjust the color, texture, position and orientation of the teeth, individually and as a group. The user manipulates the tools for these parameters and thereby generates various virtual patient models with different features and smiles.

Treatment planning icons for moving teeth are disclosed in the U.S. Pat. No. 6,648,640, which gives some idea of the types of icons and graphical user interface tools that could be used directly or adapted to simulate various parameters.

Once the user has modified the virtual patient model to achieve the patient's desired feature and smile, it is possible to automatically back-solve for the teeth, jaw and skull movement or correction necessary to achieve this result. In particular, the tooth movement necessary can be determined by isolating the teeth in the virtual patient model, treating this tooth finish position as the final position in the interactive treatment planning described in the U.S. Pat. No. 6,648,640, designing the bracket placement and virtual arch wire necessary to move teeth to that position, and then fabricating the wire and bracket placement trays, templates or jigs to correctly place the brackets at the desired location. The desired jaw movement can be determined by comparing the jaw position in the virtual patient model's finish position with the jaw position in the virtual patient model in the original condition, and using various implant devices or surgical techniques to change the shape or position of the jaw to achieve the desired position.

Tooth Displacement Measurements and Tooth Positioning

It is a common practice with orthodontists in planning treatment for a patient to prescribe craniofacial and dental changes for curing the malocclusion of the patient. The extent and type of displacements desired depend upon the nature and severity of malocclusion. Generally, the changes are prescribed in terms of craniofacial and dental displacements comprising one or more translation movements and/or one or more rotational type movements; and tooth extraction or other measures as and when necessary. The translation movements or changes are characterized in terms of mesial or distal translation, buccal or lingual translation, and occlusal (coronal) or gingival translation. The rotational type movements are characterized in terms of facial or lingual torque, mesial or distal angulation and mesial or distal rotation. During the treatment planning process, the practitioner may place the virtual teeth and the jaws of a patient in a desired position and measure the underlying changes in terms of the movements or displacements described above; or specify the values for the desired displacements and let the treatment planning software instructions position the virtual teeth and the jaws accordingly. Typically, the practitioner would simulate different virtual teeth and jaw displacement scenarios using a three-dimensional virtual dentition model of a patient on the workstation 10 of FIG. 1 before deciding upon a particular treatment strategy including craniofacial and dental displacements. These scenarios illustrate the need for a method of measuring the craniofacial and dental changes in the 3D virtual dentition model of a patient, or conversely placing the craniofacial and dental elements in desired positions in the 3D virtual dentition model of the patient as per the prescriptions for their displacements. Usually, the translation displacements are specified in mm and the torque, angulation and rotation in degrees. The preferred embodiment of the invention described herein discloses a method of measuring the virtual tooth displacements in terms of the translation, torque, angulation and rotation movements discussed above. The method produces consistent, reproducible and accurate measurements. The preferred embodiment of the invention also discloses a method enabling the user in placing/moving the virtual dental elements in positions specified by the user in terms of the translation, torque, angulation and rotation movements discussed above. There are two coordinate systems disclosed for these displacement measurements: (a) tooth axes system (TAS), and (b) a novel orthodontic reference coordinate system herein after referred to as the orthogonal curvilinear coordinate system (OCCS). These coordinate systems are described first followed by the description of individual displacement measurement and positioning methods.

Tooth Axes System

Figure 3A:
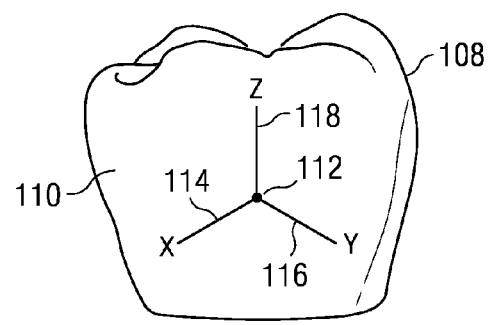
FIG. 3A illustrates the tooth axes system (TAS) for a tooth.

FIG. 3A shows the tooth axes system (TAS) 110 for the virtual tooth 108 as an example. TAS 110 comprises the origin 112, the x-axis 114 in the mesial and distal directions, the y-axis 116 in the buccal and lingual directions and the z-axis 118 in the occlusal and gingival (vertical) directions. TAS is created for each individual tooth based up on the ideal properties of the tooth in terms of its features; and is not derived from the jaw features. TAS is preferably an anatomical coordinate system for the tooth. It is preferably derived during virtual modelling of the tooth from the scanning data and the tooth templates, and is adjusted if necessary.

Figure 3B:
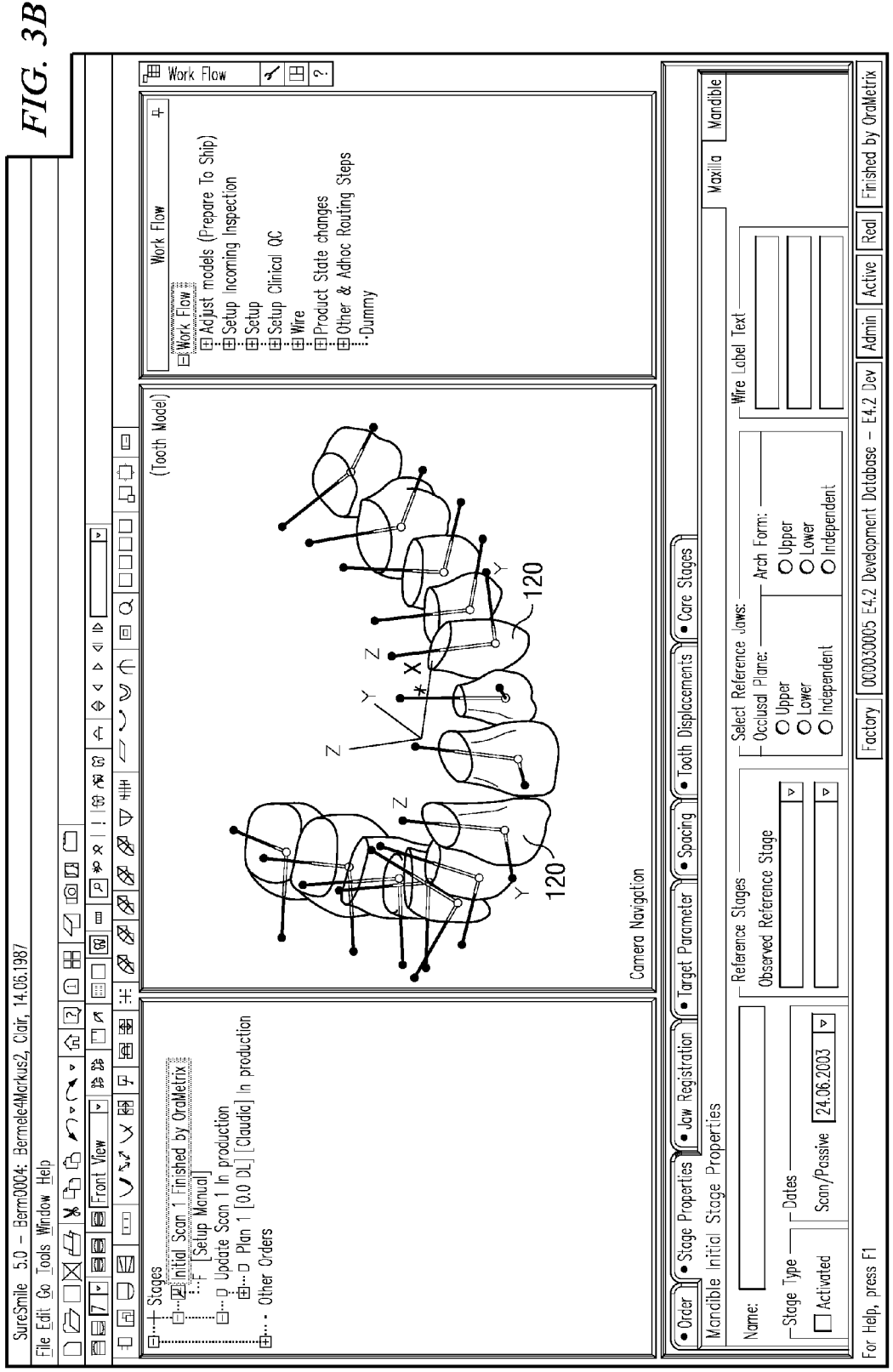
FIG. 3B shows an example of the TAS for each tooth in the maxilla of a patient.

FIG. 3B shows an example of the TAS 120 for each tooth in the maxilla of a patient. The y-axis and the z-axis of each TAS are shown in FIG. 3B; however the x-axis is not shown for simplicity sake. TAS is not related to the dental arch, so TAS for one tooth behaves independently of the TAS for another tooth. Orientation of TAS is as such not fixed in space. Indeed TAS for any tooth moves with the tooth, and its position is determined by the position of the tooth. Since TAS has no fixed relationship with the dental arch, it alone is not sufficient in providing the basis for accurate and unambiguous tooth translation displacements and rotational movements; as well as the tooth position measurements.

Orthogonal Curvilinear Coordinate System

According to a preferred embodiment of the invention, a novel orthodontic reference coordinate system herein referred to as the Orthogonal Curvilinear Coordinate System (OCCS) is disclosed that enables accurate, consistent and reproducible realization of the tooth translation displacements and rotational movements; and measurements of the virtual tooth positions discussed above. The details of the derivation of the OCCS will now be described with the help of FIGS. 3C and 3D.

The method of deriving the OCCS will now be described for the virtual teeth in the lower jaw of a patient. One skilled in the art would appreciate that a similar method would be applied to find the OCCS for the teeth in the upper jaw of the patient.

Figure 3C:
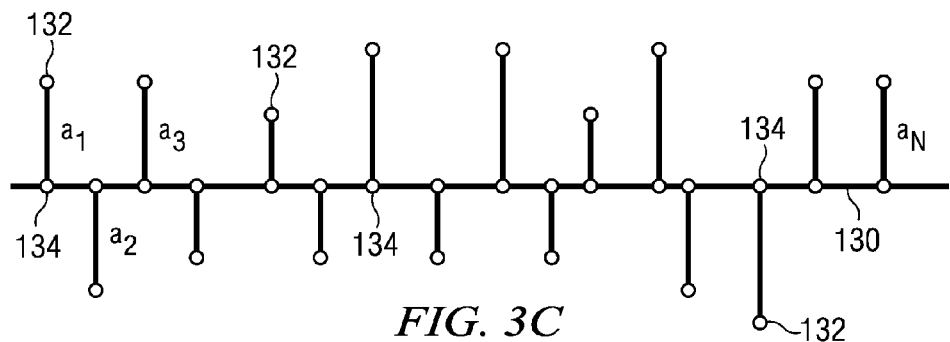
FIG. 3C illustrates the side view of a plane up on which the TAS origins for the virtual teeth in a jaw are orthogonally projected as a part of the first step in determining the orthogonal curvilinear coordinate system (OCCS), according to a preferred embodiment of the invention.

At step 1, as shown in FIG. 3C, an arbitrary plane 130 is identified such that preferably the sum of the square of the orthogonal distance for each origin 132 of the TAS for each tooth in the lower jaw from the plane 130; i.e., $a_1^2 + a_2^2 + \ldots + a_N^2$ where N is the number of teeth in the lower jaw is minimum. Alternately, the sum of the distances, i.e., $a_1 + a_2 + \ldots + a_N$ is minimized in selecting the plane 130. A side view of the plane 130 is presented in FIG. 3C so that the plane 130 appears as a line from the perspective of FIG. 3C. Orthogonal projections of the TAS origins 132 appear as the projection points 134 in FIG. 3C.

Figure 3D:
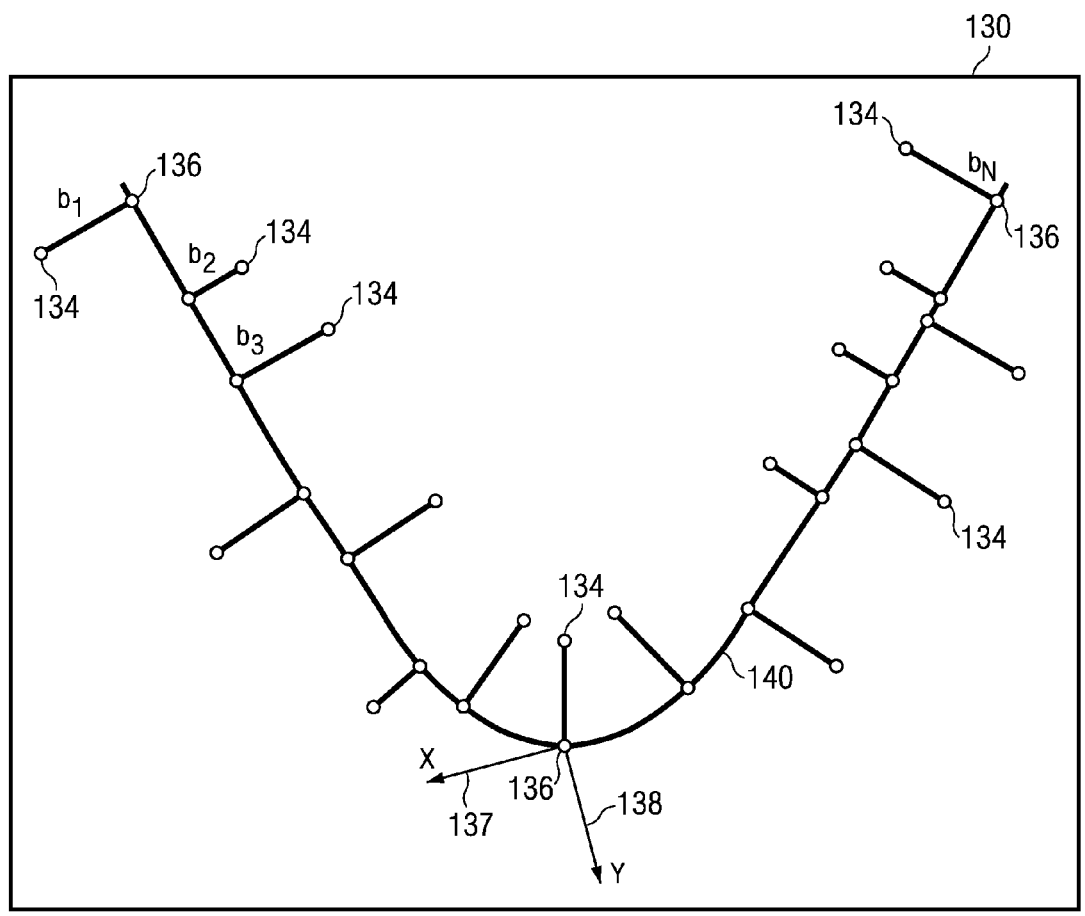
FIG. 3D illustrates the top view of the plane, shown from the side view in FIG. 3C, depicting the virtual arch (VA), the TAS origin orthogonal projection points, which are shown in FIG. 3C, and orthogonal projections on the VA of the TAS origin orthogonal projection points as a part of the second step in determining the OCCS according to a preferred embodiment of the invention.

Next, FIG. 3D shows the plane 130 as seen from the top, i.e., from the perspective of the direction orthogonal to the plane 130. In FIG. 3D, the projection points 134 are the same orthogonal projections 134 of the TAS origins shown in FIG. 3C.

At step 2, as shown in FIG. 3D, a monotonously curved virtual arch (VA) 140, preferably in the form of an even polynomial, is identified such that preferably the sum of the square of the orthogonal distance of each projection point 134 from the VA 140, i.e., $b_1^2 + b_2^2 + \ldots + b_N^2$ where N is the number of teeth in the lower jaw, is minimum. Alternately, the sum of the distances, i.e., $b_1 + b_2 + \ldots + b_N$, is minimized in selecting the VA 140. The point 136 on the VA at which the projection point 134 orthogonally meets the VA is designated the OCCS origin for the tooth.

At step 3, the OCCS coordinate axes are computed as follows: As shown in FIG. 3D, for a virtual tooth, one axis of the OCCS, e.g., x axis coincides with the tangent 137 to the VA 140 at the OCCS origin 136 for the tooth; and another axis, e.g., y axis, coincides with the normal 138 to the VA 140 at the OCCS origin 136. The z axis of the OCCS for the virtual tooth is orthogonal to the plane formed by the x axis and the y axis and is located at the OCCS origin 136 for the tooth. For the sake of keeping the clarity in the figure, neither the z axis for the OCCS, nor the virtual teeth are shown in FIG. 3D. It should be noted that the x axis, while coinciding with the tangent to the VA 140, actually follows the curved shape of the VA as it moves away from the OCCS origin; hence the name curvilinear coordinate system.

Figure 3E:
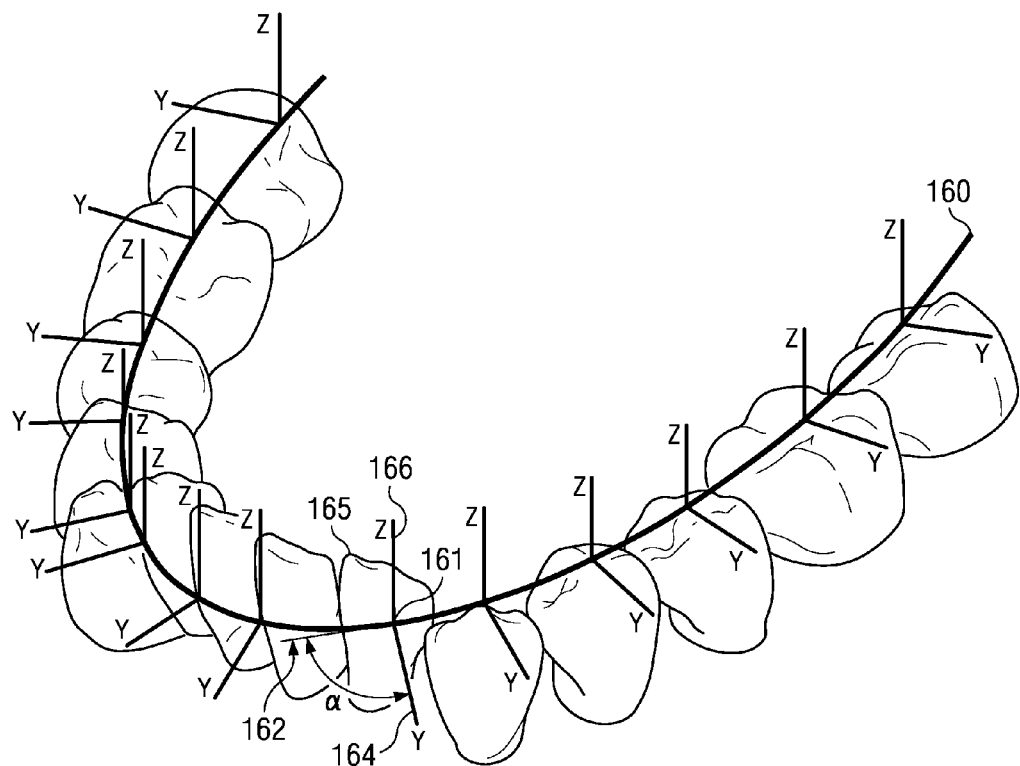
FIG. 3E presents a screen shot of an example of the OCCS for the virtual teeth in the lower jaw of a patient according to a preferred embodiment of the invention. The OCCS and the TAS are used to measure the tooth translation displacements, torque, angulation and rotation, according to a preferred embodiment of the invention.

FIG. 3E presents a screen shot of an example of the OCCS for the virtual teeth in the lower jaw of a patient according to a preferred embodiment of the invention. The OCCS is superimposed on each virtual tooth in FIG. 3E. As discussed before, the VA 160 forms the basis for constructing the OCCS for each virtual tooth in the lower jaw. As an example, for the virtual tooth 165, the point 161 on the VA is the OCCS origin; the x-axis 162 coincides with the tangent to the VA at the origin 161, the y-axis 164 coincides with the normal to VA at the origin 161 (i.e. angle α between the x-axis and the y-axis is 90°), and the z-axis 166 is perpendicular to the plane formed by the x-axis and the y-axis and passes through the origin 161. Thus, the origin 161 on the VA, the x-axis 162, the y-axis 164 and the z-axis 166 forms the OCCS for the tooth 165. Similarly, every virtual tooth has its own OCCS defined. The OCCS for a virtual tooth remains fixed as a reference for the purposes of calculating all the tooth displacement and movement measurements of the virtual tooth irrespective of the position of the tooth. The OCCS origin for a virtual tooth—also always remains at the same location on the VA for the reference purposes. However, the OCCS may also be shown at locations other than the fixed location for illustration purposes.

Figure 3F:
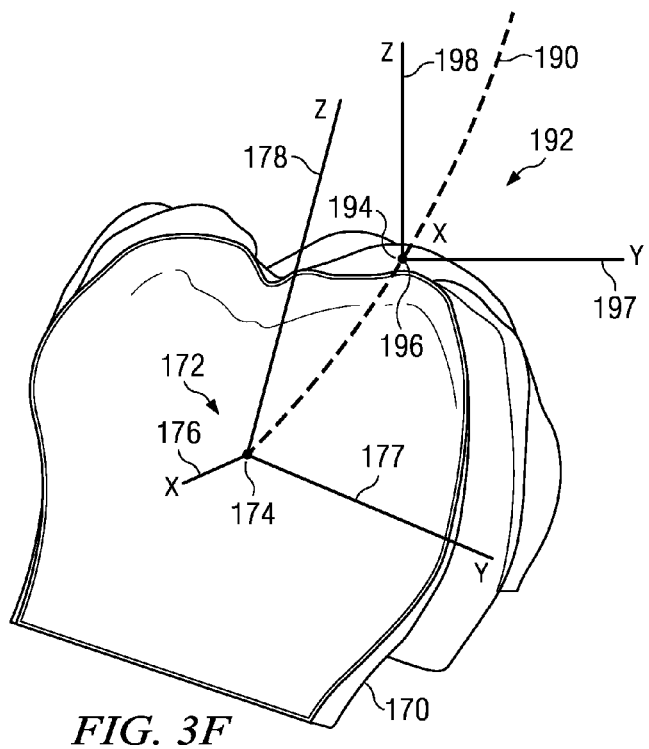
FIG. 3F illustrates the TAS and the OCCS for an example virtual tooth, according to a preferred embodiment of the invention.

FIG. 3F illustrates the TAS 172 and the OCCS 192 for an example virtual tooth 170. The TAS 172 comprises the origin 174, the x-axis 176, the y-axis 177 and the z-axis 178. The OCCS 192 is based on the VA 190 and comprises the origin 194, the x-axis 196, the y-axis 197 and the z-axis 198.

Although each virtual tooth has its own OCCS, these OCCSs are coupled together by virtue of the VA. It should be noted that the OCCS is a jaw based coordinate reference system for every tooth which imparts certain relationship between the teeth. As noted above, the OCCS does not 'move' with the tooth. In contrast, the TAS for a tooth is dependent up on the tooth geometry, and moves with the tooth as the tooth moves; and is fundamentally independent of the TAS for the other teeth. The OCCS for each virtual tooth can be used as a reference system for the virtual tooth in specifying the virtual tooth's position, and additionally in measuring any specified change in the position of the virtual tooth as compared to its position prior to the change.

When the OCCS is used for measurements, the rotation axes for the angular displacement and the torque are always in agreement with a buccolabial or a mesiodistal view of the jaw. That means the OCCS axes orient themselves by the arch, not by the single tooth. An important consequence emerges regarding the tooth root movement in connection with using the OCCS as a reference coordinate system. Due to the orientation of the OCCS axes by the VA, the possible root movements are unequivocally and distinctly perpendicular or parallel to the periodont, which gives one the option to constrain the root movement in the in-out direction (perpendicular to the VA). The use of the OCCS as a reference, and the constraint implied thereof, protects the root of any tooth from the displacements that might otherwise move the root out of the bone.

Preferably, the VA is formed as an even polynomial of higher order or any other spline approximating the arch form. That means the VA represents the arch form of a jaw and the shape of that curve can be symmetrical or asymmetrical. As discussed before, preferably the adaptation of the VA to the arch of the individual patient's teeth is done with help of the minimum sum of the distance squares between the VA points and the TAS origins using the projections onto the previously described plane containing the VA.

The use of the OCCS in conjunction with the TAS in specifying the dental positions and changes by measuring the mesial or distal translational displacements, buccal or lingual translational displacements, and occlusal (coronal) or gingival translational displacements; and the facial or lingual torque movement or displacement, mesial or distal angulation movement or displacement and mesial or distal rotation movement or displacement according to the preferred embodiments of the invention will now be described.

Mesiodistal Displacements

Figure 4:
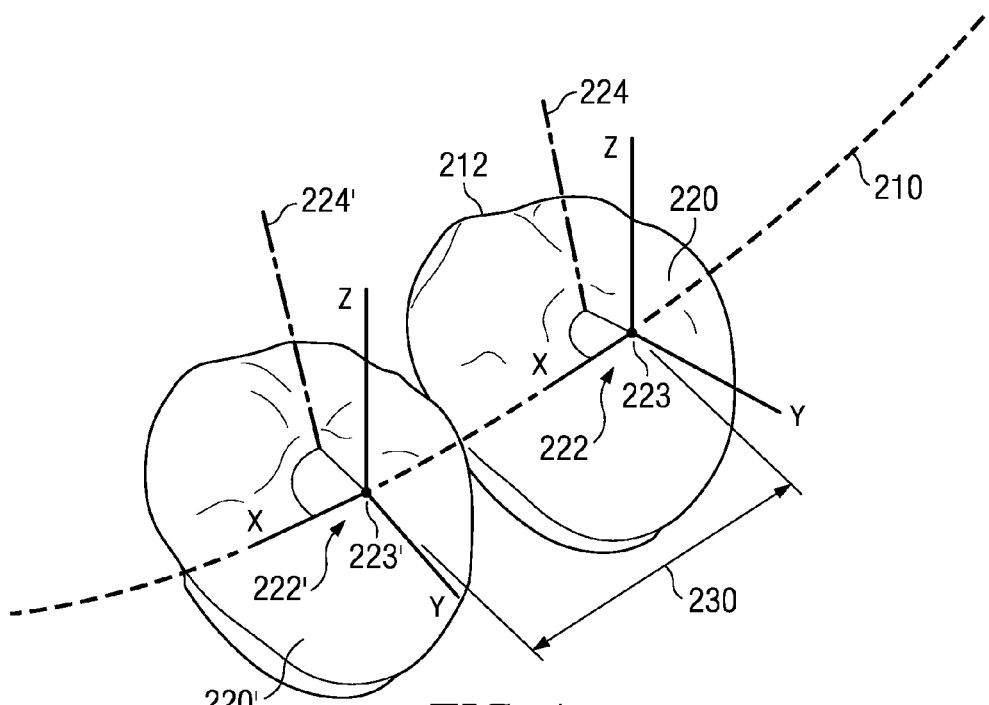
FIG. 4 illustrates the concepts of the translation measurement of the mesial displacement between the tooth in an initial position and a target position, according to a preferred embodiment of the instant invention. Measurements in the distal direction can be similarly made.

FIG. 4 illustrates the concepts of the translation measurement of the mesiodistal displacement using the OCCS according to a preferred embodiment of the instant invention. In this figure, a virtual tooth 212, a pre-molar in this example, is in an initial or malocclusion position 220 and is moved in a linear manner in the mesial direction to a new or target position 220'. The objective is to measure the mesial translation displacement between the virtual tooth positions 220 and 220'. As described earlier, the VA 210 has been determined considering the virtual tooth 212 and other virtual teeth, not shown in FIG. 4 for the sake of clarity, in the same jaw as the virtual tooth 212. The point 223 on the VA 210 is the OCCS origin for the virtual tooth 212. One skilled in the art would appreciate that the OCCS origin 223 need not be actually on or within the tooth 212. Based on the OCCS origin 223 and the VA 210, the OCCS 222, in terms of the x, y and z axes, has been determined for the virtual tooth 212. The translational displacement of the virtual tooth 212 in the mesial direction is done in a manner such that the origin 223 remains on the VA 210 while the tooth is moved, and acquires the new point position 223' on the VA 210 corresponding to the new tooth position 220'. Now, the length of the bow segment 230 along the VA 210 between the points 223 and 223' is the mesial translation displacement between the positions 220 and 220' of the virtual tooth 212. Although the OCCS 222 remains fixed for the virtual tooth 212 for the linear or translation displacement and rotational movement measurements and tooth position calculations purposes, it is shown in FIG. 4 in the new position for illustrative purposes as the OCCS 222' with the origin 223' corresponding to the tooth position 220'. Also shown in FIG. 4 for illustrative purpose is the z-axis 224 of the TAS for the virtual tooth 212 in the position 220 and the z-axis 224' of the TAS as it would appear for the tooth position 220'. For the sake of clarity of the figure, the x and y axes for the TAS are not shown in FIG. 4. The x, y and z axes for the OCCS 222 and 222' are shown in FIG. 4. Although FIG. 4 illustrates the concepts of the translation measurement of the mesial displacement for a tooth in two positions, i.e., between an initial position and a target position, the procedure described above can also be applied to measure the mesial displacement of a tooth in a particular position of interest with respect to the OCCS. In that sense, one skilled in the art would understand that the mesial displacement of the tooth in the initial position 220 is zero from the origin 223 of the OCCS 220; and in the target position 220' is the length of the bow segment 230 from the origin 223 of the OCCS 220. One skilled in the art would appreciate that the tooth translation displacement in the distal direction can be measured in a manner similar to the measurement in the mesial direction described above.

In summary then, the mesiodistal displacement of a tooth in a given position is measured, using the OCCS for the tooth, as the length of the bow segment along the VA between the OCCS origin and the position of the tooth. The procedure can be repeated for the tooth in an initial position and then in a target position to calculate the mesiodistal displacement in each case and the difference between the two displacement measurements would be the relative displacement between the two positions of the tooth. One skilled in the art would appreciate that a similar procedure can be used to position a tooth at a desired mesiodistal displacement with respect to the tooth's OCCS origin by moving the tooth to the position whose distance measured in terms of the length of the bow segment along the VA from the OCCS origin is equal to the desired mesiodistal displacement. Similarly, a tooth can be moved from its initial position to a target positon at a desired mesiodistal displacement from the initial position using the OCCS so that the length of the bow segment along the VA measured from the initial position to the target position is equal to the desired mesiodistal displacement.

It should be noted that the tooth TAS position relative to its OCCS is not changed by a shift of the tooth along the VA as discussed above. Thus the magnitude of the shift of the tooth with respect to the reference system OCCS is an appropriate measure for the mesiodistal tooth shift. One skilled in the art would appreciate that this length is better apt to represent the actual covered tooth path than the Euclidean distance.

Buccolingual and Coronal-Gingival Displacements

Figure 5A:
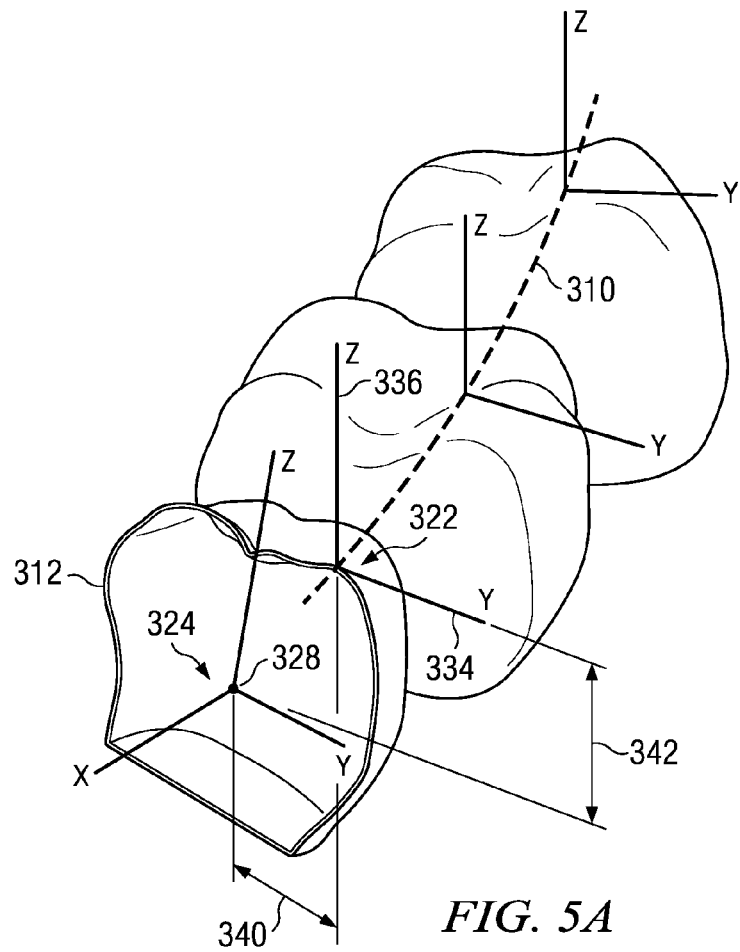
FIG. 5A illustrates the concepts of translation measurement of the buccolingual and coronal-gingival displacements for a particular tooth position with respect to the OCCS, according to a preferred embodiment of the instant invention.

FIG. 5A illustrates the concepts of the translation measurement in terms of the buccolingual and coronal-gingival displacements of a particular tooth position with respect to its OCCS according to the preferred embodiment of the instant invention. In this figure, the VA 310 is used to define the OCCS based upon the concepts described earlier. Solely for the ease of illustration, the VA 310 has been shifted in the buccal-coronal (or occlusal) direction. For the virtual tooth 312, the OCCS 322 and the TAS 324 provide the basis for measuring the position of the tooth with respect to the buccolingual and coronal-gingival displacements from the OCCS. The buccal displacement 340 for the virtual tooth 312 is the orthogonal distance between the plane which contains the z-axis 336 of the OCCS 322 (z-axis plane) and the plane which contains the origin 328 of the TAS 324 for the tooth 312 and is parallel to the z-axis plane. One skilled in the art would appreciate that if the virtual tooth is positioned in the lingual direction, then the lingual displacement of the tooth with respect to the OCCS can be similarly measured. The coronal displacement 342 in this case for the virtual tooth 312 is the distance between the plane which contains the y-axis 334 of the OCCS 322 (y-axis plane) and the plane which contains the origin 328 of the TAS 324 and is parallel to the y-axis plane. One skilled in the art would appreciate that the when the virtual tooth is positioned in the gingival direction the gingival displacement can be similarly measured. In other words, the buccolingual distance of a tooth from the OCCS is equivalent to the distance of the TAS normal to the VA, projected into the respective reference plane. Therefore, the translation of a tooth that moves in this direction is given by the parameter difference in the start and end positions of the virtual tooth. These concepts are further described using FIGS. 5B and 5C below.

Figure 5B:
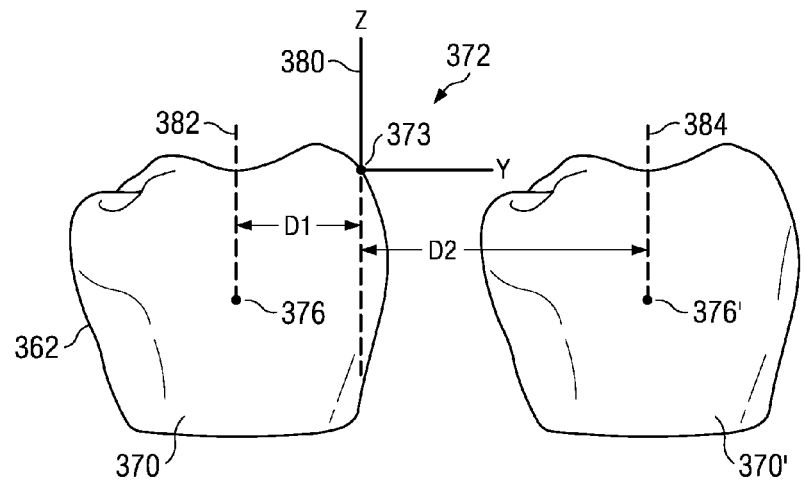
FIG. 5B further illustrates the concepts of the translation measurement of the buccolingual displacement of a virtual tooth between an initial position and a target position using the OCCS, according to a preferred embodiment of the instant invention.

FIG. 5B further illustrates the concepts of the translation measurement of the buccolingual displacement of a virtual tooth from an initial position to a target position using the OCCS, according to a preferred embodiment of the instant invention. In this figure, a virtual tooth 362 is in an initial or malocclusion position 370 and is moved in a linear manner in the buccal direction to a new or target position 370'. The objective is to measure the buccal translation displacement between the virtual tooth positions 370 and 370'. As described earlier, the OCCS 372 has been determined for the virtual tooth 362. The point 373 is the origin for the OCCS 372. The y-axis and the z-axis for the OCCS 372 are shown in FIG. 5B. The view in FIG. 5B is from the perspective of the x-axis, so the x-axis is not shown. The buccal displacement for the virtual tooth 362 in the position 370 is the orthogonal distance D1 between the plane 380, which contains the z-axis of the OCCS 372 (z-axis plane), and the plane 382, which contains the origin 376 of the TAS for the tooth 362 in the position 370 and is parallel to the z-axis plane. Similarly, the buccal displacement for the virtual tooth 362 in the position 370' is the orthogonal distance D2 between the z-axis plane 380 and the plane 384 which contains the origin 376' of the TAS for the tooth 362 in the position 370' and is parallel to the z-axis plane. Since D1 and D2 are on different sides of the z-axis plane 380, the buccal displacement between the tooth positions 370 and 370' is equal to D1+D2. On the other hand, one skilled in the art would appreciate that, if D1 and D2 were on the same side of the z-axis plane, then the buccal displacement between the tooth positions 370 and 370' would be the appropriate difference between D1 and D2 (i.e. D2–D1 or D1–d2). One skilled in the art would appreciate that the tooth translation displacement in the lingual direction can be similarly measured.

In summary then, the buccolingual displacement of a tooth in a given position is measured, using the OCCS for the tooth, as the orthogonal distance between the plane which contains the z-axis of the OCCS (z-axis plane) and the plane which contains the origin of the TAS for the tooth and is parallel to the z-axis plane. The procedure can be repeated for the tooth in an initial position and then in a target position to calculate the buccolingual displacement in each case; and the appropriate sum of or the difference between the two displacement measurements would be the relative displacement between the two positions of the tooth. One skilled in the art would appreciate that a similar procedure can be used to position a tooth at a desired buccolingual displacement with respect to the tooth's OCCS by moving the tooth to the position whose buccolingual distance measured in terms of the orthogonal distance between the plane which contains the z-axis of the OCCS (z-axis plane) and the plane which contains the origin of the TAS for the tooth and is parallel to the z-axis plane is equal to the desired buccolingual displacement. Similarly, a tooth can be moved from its initial position to a target position at a desired buccolingual displacement from the initial position using the OCCS so that the orthogonal distance between the first plane containing the origin of the TAS for the tooth in the initial position and the second plane containing the origin of the TAS for the tooth in the target position, both the first plane and the second plane being parallel to the OCCS z-axis plane, is equal to the desired buccolingual displacement.

Figure 5C:
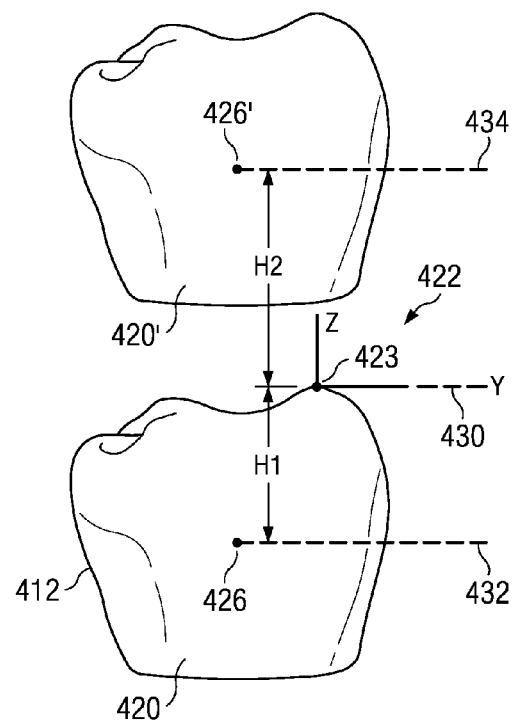
FIG. 5C further illustrates the concepts of the translation measurement of the coronal-gingival displacement of a virtual tooth between an initial position and a target position using the OCCS, according to a preferred embodiment of the instant invention.

FIG. 5C further illustrates the concepts of the translation measurement of the coronal (occlusal)-gingival displacement of a virtual tooth from an initial position to a target position using the OCCS, according to a preferred embodiment of the instant invention. In this figure, a virtual tooth 412 is in an initial or malocclusion position 420 and is moved in a linear manner in the coronal direction to a new or target position 420'. The objective is to measure the coronal translation displacement between the virtual tooth positions 420 and 420'. As described earlier, the OCCS 422 has been determined for the virtual tooth 412. The point 423 is the origin for the OCCS 422. The y-axis and the z-axis for the OCCS 422 are shown in FIG. 5C. The view in FIG. 5C is from the perspective of the x-axis, so the x-axis is not shown. The coronal displacement for the virtual tooth 412 in the position 420 is the orthogonal height H1 between the plane 430 containing the y-axis of the OCCS 422 (y-axis plane) and the plane 432 parallel to the y-axis plane 430 and containing the origin 426 of the TAS for the tooth 412 in the position 420. Similarly, the coronal displacement for the virtual tooth 412 in the position 420' is the orthogonal height H2 between the y-axis plane 430 and the plane 434 parallel to the y-axis plane 430 and containing the origin 426' of the TAS for the tooth 412 in the position 420'. Since H1 and H2 are on different sides of the y-axis plane, the coronal displacement between the tooth positions 420 and 420' is equal to H1+H2. On the other hand, one skilled in the art would appreciate that, if H1 and H2 were on the same side of the y-axis plane, then the coronal displacement between the tooth positions 420 and 420' would be the appropriate difference between H1 and H2.

One skilled in the art would appreciate that the tooth translation displacement in the gingival direction can be similarly measured.

In summary then, the coronal-gingival displacement of a tooth in a given position is measured, using the OCCS for the tooth, as the orthogonal distance between the plane which contains the y-axis of the OCCS (y-axis plane) and the plane which contains the origin of the TAS for the tooth and is parallel to the y-axis plane. The procedure can be repeated for the tooth in an initial position and then in a target position to calculate the coronal-gingival displacement in each case; and the appropriate sum of or the difference between the two displacement measurements would be the relative displacement between the two positions of the tooth. One skilled in the art would appreciate that a similar procedure can be used to position a tooth at a desired coronal-gingival displacement with respect to the tooth's OCCS by moving the tooth to the position whose coronal-gingival distance measured in terms of the orthogonal distance between the plane which contains the y-axis of the OCCS (y-axis plane) and the plane which contains the origin of the TAS for the tooth and is parallel to the y-axis plane is equal to the desired coronal-gingival displacement. Similarly, a tooth can be moved from its initial position to a target position at a desired coronal-gingival displacement from the initial position using the OCCS so that the orthogonal distance between the first plane containing the origin of the TAS for the tooth in the initial position and the second plane containing the origin of the TAS for the tooth in the target position, both the first plane and the second plane being parallel to the OCCS y-axis plane, is equal to the desired coronal-gingival displacement.

By analogy, the coronal-gingival distance is the distance of the TAS center or origin from the reference plane (the plane, in which the VA has been defined). The translation of a tooth in this direction is calculated again as the difference of the distances in the start and end positions of the virtual tooth.

Occlusal displacement of a virtual tooth is another way of expressing the coronal displacement with the same value.

Torque

Figure 6A:
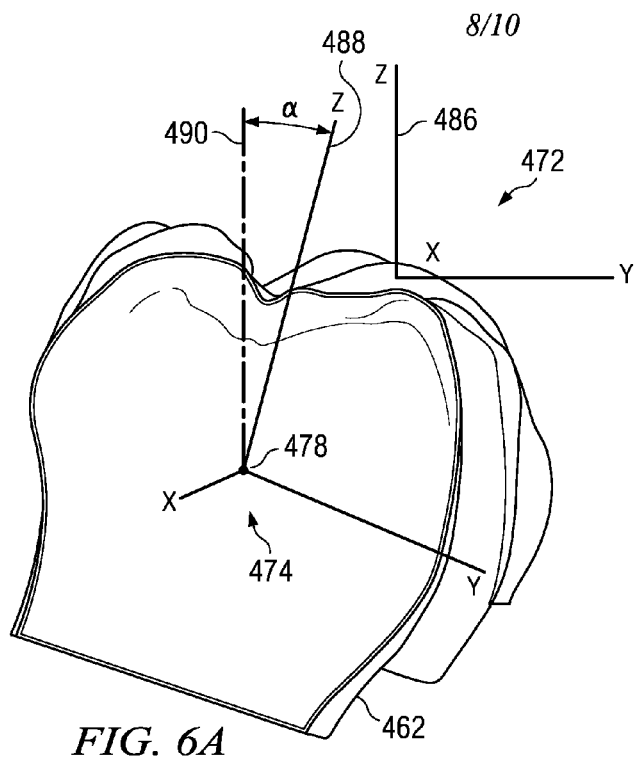
FIG. 6A illustrates the concepts of the torque measurement for a virtual tooth in a particular position, according to a preferred embodiment of the instant invention.

FIG. 6A illustrates the concepts of the torque measurement according to a preferred embodiment of the instant invention. For the ease of illustration VA is not shown in this figure. The principles of the torque measurements are illustrated by way of the example virtual tooth 462, which is sliced using a clipping plane tool in order to better illustrate the measurements. The OCCS 472, shown as though viewed from the perspective of the x-axis direction in FIG. 6A for the ease of illustration, and the TAS 474, both for the virtual tooth 462, form the basis for calculating the torque for the virtual tooth 462 in the particular tooth position. Torque for the virtual tooth 462 is measured in degrees as the angle α between the z-axis 488 of the TAS 474 and the line 490 which passes through the origin 478 of the TAS 474 and is drawn parallel to the z-axis 486 of the OCCS 472.

Figure 6B:
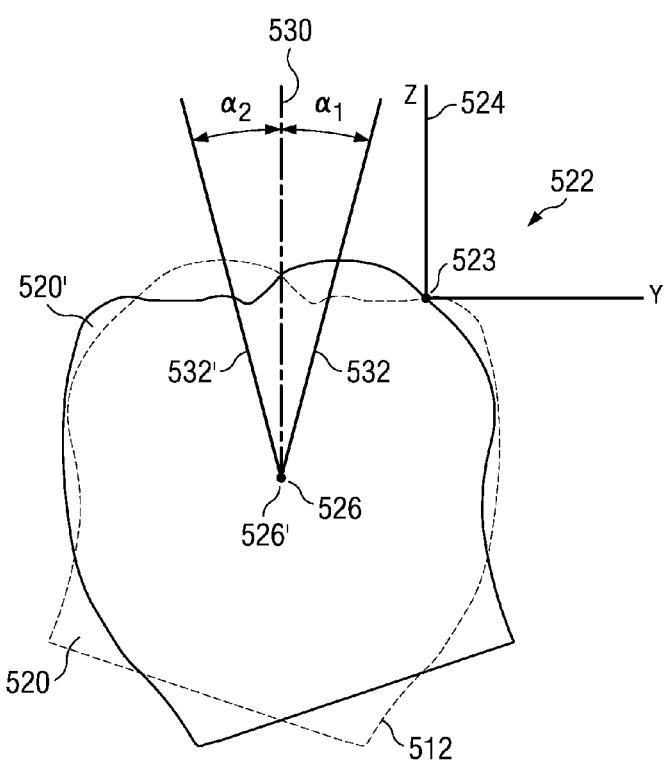
FIG. 6B further illustrates the concepts of the torque measurement between an initial position of a virtual tooth and a target position using the OCCS, according to a preferred embodiment of the instant invention.

FIG. 6B further illustrates the concepts of the torque measurement between an initial position of a virtual tooth and a target position using the OCCS, according to a preferred embodiment of the instant invention. In this figure, a virtual tooth 512 is in an initial or malocclusion position 520 (shown in the dotted lines) and is given a torque (rotated around the x axis of the OCCS) in order to bring it to a new or target position 520' (shown in the solid lines). The objective is to measure the torque between the virtual tooth positions 520 and 520'. As described earlier, the OCCS 522 has been determined for the virtual tooth 512. The point 523 is the origin for the OCCS 522. The y-axis and the z-axis for the OCCS 522 are shown in FIG. 6B. The view in FIG. 6B is from the perspective of the x-axis, so the x-axis is not shown. The procedure described above with reference to FIG. 6A is applied to calculate the torque for the tooth positions 520 and 520'. The torque for the tooth position 520 is the angle $\alpha_1$ between the z-axis 532 of the TAS for the tooth position 520 and the line 530 which passes through the origin 526 of the TAS for the tooth position 520 and is drawn parallel to the z-axis 524 of the OCCS 522. Similarly, the torque for the tooth position 520' is the angle $\alpha_2$ between the z-axis 532' of the TAS for the tooth position 520' and the line 530 which passes through the origin 526' of the TAS for the tooth position 520' and is drawn parallel to the z-axis 524 of the OCCS 522. For the ease of illustration the TAS origin point 526' is shown at the same location as the TAS origin point 526 in FIG. 6B, which need not always be the case depending upon the combination of displacements the tooth 520 may have been subjected to. Since the angles $\alpha_1$ and $\alpha_2$ are on either side of the line 530 parallel to the OCCS z axis, the total torque in this case is the angle $\alpha = \alpha_1 + \alpha_2$. If on the other hand, the angles $\alpha_1$ and $\alpha_2$ were on the same side of the line 530, then total torque would be the appropriate difference between the angles $\alpha_1$ and $\alpha_2$.

In summary then, the torque for a tooth in a given position is measured, using the OCCS for the tooth, in degrees as the angle α between the z-axis of the TAS for the tooth and the line which passes through the origin of the TAS and is drawn parallel to the z-axis of the OCCS, when viewed from the perspective of the x-axis direction of the OCCS. The procedure can be repeated for the tooth in an initial position and then in a target position to calculate the torque in each case; and the appropriate sum of, or the difference between, the two torque measurements would be the relative torque between the two positions of the tooth. One skilled in the art would appreciate that a similar procedure can be used to position a tooth at a desired torque with respect to the tooth's OCCS by moving the tooth to the position whose torque measured in degrees as the angle α between the z-axis of the TAS for the tooth and the line which passes through the origin of the TAS and is drawn parallel to the z-axis of the OCCS is equal to the desired torque, when viewed from the perspective of the x-axis direction of the OCCS. Similarly, a tooth can be moved from its initial position to a target position having the desired torque with respect to the initial position using the OCCS and TAS.

In other words, the inclination of the TAS relative to the OCCS from a mesial view is given by the visible angle between the vertical axes of both the systems. The mesial view is defined by the tangent at the VA at the origin of the OCCS, i.e. x-axis for the OCCS. The torque or the corresponding tooth rotation around the x-axis for the OCCS results again from the difference of the inclinations in the virtual tooth start and end positions.

Angulation

Figure 7A:
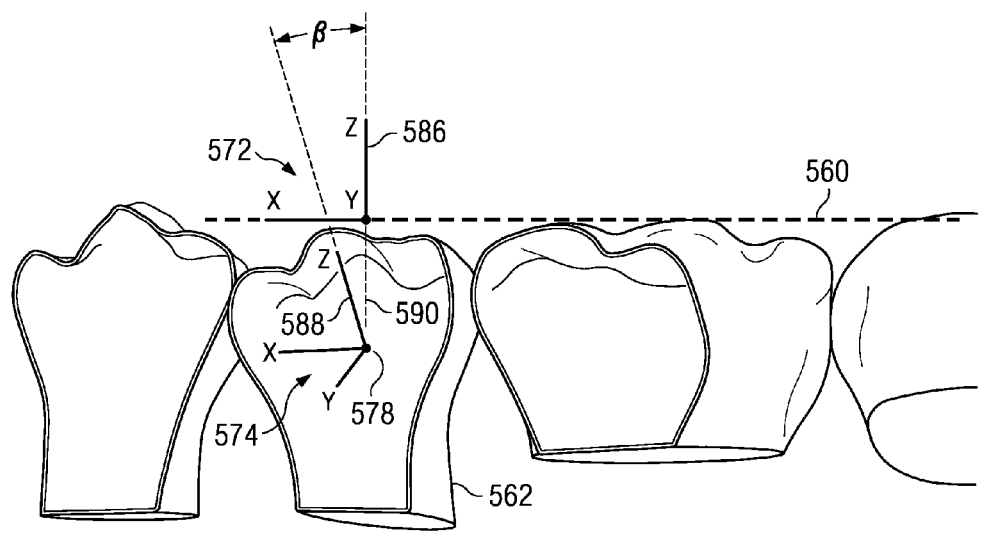
FIG. 7A illustrates the concepts of the angulation measurement for a virtual tooth in a particular position, according to a preferred embodiment of the instant invention.

FIG. 7A illustrates the concepts of the angulation measurement for a virtual tooth in a particular position, according to a preferred embodiment of the instant invention. For the ease of illustration, VA 560 is shown as being viewed from the direction of the y-axis of the OCCS and shifted slightly in the z-axis direction of the OCCS in this figure. The principles of the angulation measurements are illustrated by way of the example virtual tooth 562 which is sliced using a clipping plane tool in order to better illustrate the measurements. The OCCS 572 and the TAS 574, both for the virtual tooth 562, form the basis for calculating the angulation for the virtual tooth 562. Angulation for the virtual tooth 562 is measured in degrees as the angle β between the z-axis 588 of the TAS 574 and the line 590 which passes through the origin 578 of the TAS 574 and is drawn parallel to the z-axis 586 of the OCCS 572. Coincidently, in FIG. 7A, due to the particular orientation of the figure the OCCS z-axis 586 and the TAS origin 578 appear to fall on the same line; however that is not always the case.

Figure 7B:
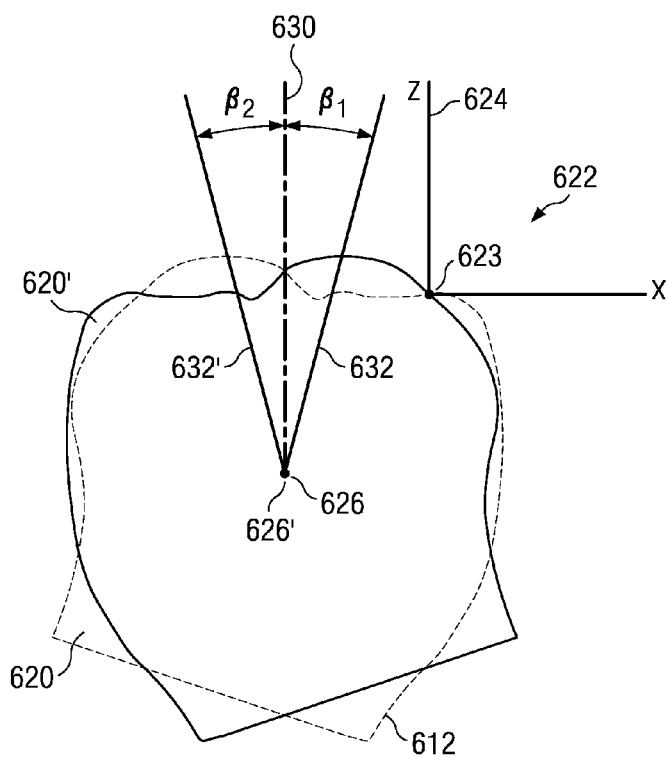
FIG. 7B further illustrates the concepts of the angulation measurement between an initial position of a virtual tooth and a target position using the OCCS, according to a preferred embodiment of the instant invention.

FIG. 7B further illustrates the concepts of the angulation measurement between an initial position of a virtual tooth and a target position using the OCCS, according to a preferred embodiment of the instant invention. In this figure, a virtual tooth 612 is in an initial or malocclusion position 620 (shown in the dotted lines) and is given an angulation (rotated around the y-axis of the OCCS) in order to bring it to a new or target position 620' (shown in the solid lines). The objective is to measure the angulation between the virtual tooth positions 620 and 620'. As described earlier, the OCCS 622 has been determined for the virtual tooth 612. The point 623 is the origin for the OCCS 622. The x-axis and the z-axis for the OCCS 622 are shown in FIG. 7B. The view in FIG. 7B is from the perspective of the y-axis, so the y-axis is not shown. The procedure described above with reference to FIG. 7A is applied to calculate the angulation for the tooth positions 620 and 620'. The angulation for the tooth position 620 is the angle $\beta_1$ between the z-axis 632 of the TAS for the tooth position 620 and the line 630 which passes through the origin 626 of the TAS for the tooth position 620 and is drawn parallel to the z-axis 624 of the OCCS 622. Similarly, the angulation for the tooth position 620' is the angle $\beta_2$ between the z-axis 632' of the TAS for the tooth position 620' and the line 630 which passes through the origin 626' of the TAS for the tooth position 620' and is drawn parallel to the z-axis 624 of the OCCS 622. For the ease of illustration, the TAS origin point 626' is shown at the same location as the TAS origin point 626 in FIG. 7B, which need not always be the case depending upon the combination of displacements the tooth 620 may have been subjected to. Since the angles $\beta_1$ and $\beta_2$ are on either side of the line 630 parallel to the OCCS z axis, the total angulation in this case is the angle $\beta=\beta_1+\beta_2$. If on the other hand, the angles $\beta_1$ and $\beta_2$ were on the same side of the line 630, then total angulation would be the appropriate difference between the angles $\beta_1$ and $\beta_2$.

In summary then, the angulation for a tooth in a given position is measured, using the OCCS for the tooth, in degrees as the angle $\beta$ between the z-axis of the TAS for the tooth and the line which passes through the origin of the TAS and is drawn parallel to the z-axis of the OCCS, when viewed from the perspective of the y-axis direction of the OCCS. The procedure can be repeated for the tooth in an initial position and then in a target position to calculate the angulation in each case; and the appropriate sum of, or the difference between, the two angulation measurements would be the relative angulation between the two positions of the tooth. One skilled in the art would appreciate that a similar procedure can be used to position a tooth at a desired angulation with respect to the tooth's OCCS by moving the tooth to the position whose angulation measured in degrees as the angle $\beta$ between the z-axis of the TAS for the tooth and the line which passes through the origin of the TAS and is drawn parallel to the z-axis of the OCCS is equal to the desired angulation, when viewed from the perspective of the y-axis direction of the OCCS. Similarly, a tooth can be moved from its initial position to a target position having the desired angulation with respect to the initial position using the OCCS and TAS.

In other words, similar to the torque the inclination angle or the angulation of the vertical axes is determined from a buccolabial view. This line of vision is also orientated by the VA and matches the usual perspective when e.g. estimating a plaster model. The angular movement of a virtual tooth is calculated also from the angle difference in the start and end position of the virtual tooth.

Rotation

Figure 8A:
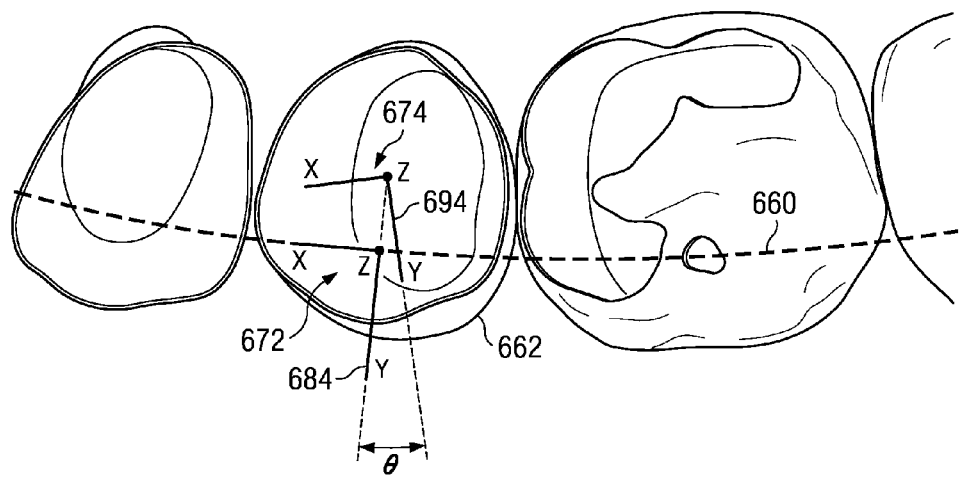
FIG. 8A illustrates the concepts of the rotation measurement for a virtual tooth in a particular position, according to a preferred embodiment of the instant invention.

FIG. 8A illustrates the concepts of the rotation measurement for a virtual tooth in a particular position according to the preferred embodiment of the instant invention. It should be noted that the method of measuring the rotation is different from that for torque and angulation since it is not possible to describe the rotation around simply one axis of the OCCS independently from other movements. For example, if the vertical (or z) axis is selected as the rotation axis, and the vertical axes of the TAS and the OCCS are inclined relative to each other, a rotation around the vertical axis would result in a nutation of the tooth root; and torque and angulation would be periodically transformed into each other. Such a result would be unacceptable. Therefore, according to a preferred embodiment of the invention, the angle between the y-axes of both coordinate systems is chosen for measurement of the rotation after transformation of the TAS is done in such a way that its vertical axis becomes parallel to that of the OCCS. In other words, the transformation makes the vertical (z) axis of the TAS perpendicular to the x-y plane of the OCCS. The transformation is executed in such measure that both axes are rotated onto each other in the shortest way. That means, angulation and torque are compensated before rotation is measured. In FIG. 8A, the VA 660 is used to define the OCCS based upon the concepts described earlier. The principles of the rotation measurements are illustrated by way of the example virtual tooth 662, which is sliced using a clipping plane tool in order to better illustrate the measurements. The OCCS 672 and the TAS 674, both for the virtual tooth 662, form the basis for calculating the rotation for the virtual tooth 662. Prior to making the rotation measurement, the TAS 674 is transformed in a manner such that the z-axis of the TAS 674 is parallel to the z-axis of the OCCS 672. These z-axes are not visible in FIG. 8A, as the virtual teeth are displayed as though viewed from the perspective of the z-axis of the OCCS 672. Now, the rotation for the virtual tooth 662 is measured in degrees as the angle $\theta$ between the y-axis 684 of the OCCS and the y-axis 694 of the TAS 674. If the rotation is calculated as the difference between the angles of the start and end positions of a virtual tooth, then the measurement actually represents the virtual tooth rotation around its own TAS axis.

Figure 8B:
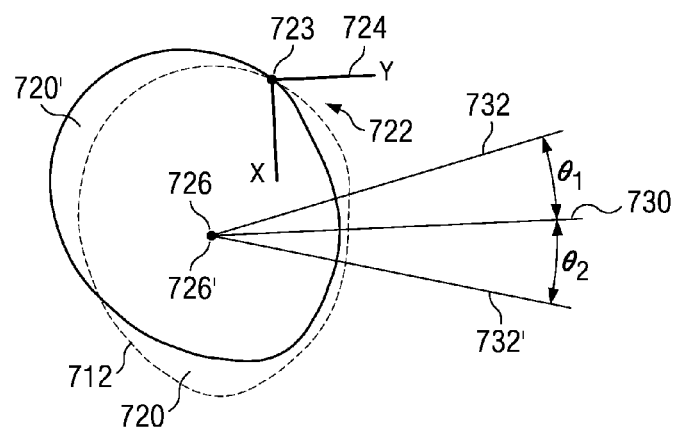
FIG. 8B further illustrates the concepts of the rotation measurement between an initial position of a virtual tooth and a target position using the OCCS, according to a preferred embodiment of the instant invention.

FIG. 8B further illustrates the concepts of the rotation measurement between an initial position of a virtual tooth and a target position using the OCCS, according to a preferred embodiment of the instant invention. In this figure, a virtual tooth 712 is in an initial or malocclusion position 720 (shown in the dotted lines) and is given an rotation (rotated around the z-axis of the OCCS) in order to bring it to a new or target position 720' (shown in the solid lines). The objective is to measure the rotation between the virtual tooth positions 720 and 720'. As described earlier, the OCCS 722 has been determined for the virtual tooth 712. The point 723 is the origin for the OCCS 722. The x-axis and the y-axis for the OCCS 722 are shown in FIG. 8B. The view in FIG. 8B is from the perspective of the z-axis, so the z-axis is not shown. The procedure described above with reference to FIG. 8A is applied to calculate the rotation for the tooth positions 720 and 720'. The TAS for the tooth position 720 and the TAS for the tooth position 720' each is transformed such that the z-axis for each TAS is parallel to the z-axis of the OCCS. The rotation for the tooth position 720 is the angle $\theta_1$ between the y-axis 732 of the TAS for the tooth position 720 and the line 730 which passes through the origin 726 of the TAS for the tooth position 720 and is drawn parallel to the y-axis 724 of the OCCS 722. Similarly, the rotation for the tooth position 720' is the angle $\theta_2$ between the y-axis 732' of the TAS for the tooth position 720' and the line 730 which passes through the origin 726' of the TAS for the tooth position 720' and is drawn parallel to the y-axis 724 of the OCCS 722. For the ease of illustration, the TAS origin point 726' is shown at the same location as the TAS origin point 726 in FIG. 8B, which need not always be the case depending upon the combination of displacements the tooth 720 may have been subjected to. Since the angles $\theta_1$ and $\theta_2$ are on either side of the line 730 parallel to the OCCS y-axis, the total rotation in this case is the angle $\theta=\theta_1+\theta_2$. If on the other hand, the angles $\theta_1$ and $\theta_2$ were on the same side of the line 730, then total rotation would be the appropriate difference between the angles $\theta_1$ and $\theta_2$.

In summary then, the rotation for a tooth in a given position is measured, using the OCCS and the TAS for the tooth, once the TAS has been transformed such that the z-axis of the TAS is parallel to the z-axis of the OCCS, in degrees as the angle $\theta$ between the y-axis of the OCCS and the y-axis of the TAS, when viewed from the perspective of the z-axis direction of the OCCS. The procedure can be repeated for the tooth in an initial position and then in a target position to calculate the rotation in each case; and the appropriate sum of, or the difference between, the two rotation measurements would be the relative rotation between the two positions of the tooth. One skilled in the art would appreciate that a similar procedure can be used to position a tooth at a desired rotation with respect to the tooth's OCCS, once the tooth TAS has been transformed as described above, by moving the tooth to the position whose rotation measured in degrees as the angle $\theta$ between the y-axis of the OCCS and the y-axis of the TAS is equal to the desired rotation, when viewed from the perspective of the z-axis direction of the OCCS. Similarly, a tooth can be moved from its initial position to a target position having the desired rotation with respect to the initial position using the OCCS and transformed TAS.

One skilled in the art would appreciate that multiple displacements involving translation movements and the rotational type movements (e.g. torque, angulation and rotation) of a tooth can be measured with the procedures described above. Given tooth positions can be measured as well as tooth can be positioned as desired with the help of OCCS and TAS using the procedures disclosed herein. The procedures can be applied to one or more virtual teeth in a jaw as desired during treatment planning.

The coordinate systems comprising the TAS and the OCCS; and the methods of measuring the translation displacements such as mesiodistal displacement, buccolingual displacement and coronal-gingival displacement; and torque, angulation and rotation described above are implemented via software instructions in the workstation 10 of FIG. 1, and can be used in conjunction with other elements of the system 100 of FIG. 1. As discussed above, it is a common practice with orthodontists in planning treatment for a patient to prescribe craniofacial and dental changes for curing the malocclusion of the patient. The extent and type of displacements desired depend upon the nature and severity of malocclusion. Generally, the changes are prescribed in terms of craniofacial and dental displacements comprising one or more translation movements and/or one or more rotational type movements; and tooth extraction or other measures as and when necessary. The translation movements or changes are characterized in terms of mesial or distal translation, buccal or lingual translation, and occlusal (coronal) or gingival translation. The rotational type movements are characterized in terms of facial or lingual torque, mesial or distal angulation and mesial or distal rotation. During the treatment planning process, the practitioner may place the virtual teeth and the jaws of a patient in a desired position and measure the underlying changes in terms of the movements or displacements described above; or specify the values for the desired displacements and let the treatment planning software instructions position the virtual teeth and the jaws accordingly. Typically, the practitioner would simulate different virtual teeth and jaw displacement scenarios using a 3D virtual dentition model of a patient on the workstation 10 of FIG. 1 before deciding upon a particular treatment strategy including crainofacial and dental displacements. As discussed above, the workstation 10 provides software instructions for measuring the craniofacial and dental changes in the 3D virtual dentition model of a patient, or conversely placing the craniofacial and dental elements in desired positions in the 3D virtual dentition model of the patient as per the prescriptions for their displacements. The workstation 10 provides software instructions for measuring the virtual crainofacial and dental displacements in terms of the translation, torque, angulation and rotation movements discussed above. The workstation 10 additionally includes software instructions that enable an user in placing/moving the virtual craniofacial and dental elements in positions specified by the user in terms of the translation, torque, angulation and rotation movements discussed above using virtual 3D dentition model of a patient. Additionally, the system 100 of FIG. 1 enables a user in sharing the treatment planning information with and communicating the craniofacial and dental displacement measurements and positions to other clinics and specialists via the communication media 37 which may comprise internet, wireless communications and other communication media and structures.

One skilled in the art would appreciate that, following the orthodontic conventions and without loss of generality, one would assign the positive values to the measurements of the translation displacements in the mesial, buccal and coronal (or occlusal) directions, and negative values to the measurements of the displacements in the distal, lingual and gingival directions. Similarly, the torque measurements are assigned the positive values in the facial direction and the negative values in the lingual directions; and the angulation and rotation measurements are each assigned the positive values in the mesial direction and the negative values in the distal directions.

Presently preferred and alternative embodiments of the invention have been set forth. Variation from the preferred and alternative embodiments may be made without departure from the scope and spirit of this invention.

We claim:

1. A method of measuring displacement of a virtual three-dimensional tooth for treatment planning using a workstation, comprising the steps of:
   (a) obtaining a virtual three-dimensional model of each tooth in a jaw of a patient in an initial state;
   (b) selecting a tooth origin for said each tooth; wherein said tooth origin for said each tooth is selected based upon anatomical structure of said each tooth; wherein said tooth origin for said each tooth remains fixed on said each tooth;
   (c) finding a reference virtual arch based upon location of said tooth origin for said each tooth;
       wherein said reference virtual arch is contained in an arbitrary plane;
       wherein said arbitrary plane is located based upon location of said tooth origin for said each tooth;
       wherein said reference virtual arch is shaped in a monotonous curve;
   (d) finding a tooth axes system for said each tooth; wherein said tooth axes system comprises said tooth origin for said tooth, a tooth x-axis in mesial and distal directions of said tooth, a tooth y-axis in buccal and lingual directions of said tooth and a tooth z-axis in occlusal and gingival directions of said tooth; wherein said tooth axes system for said each tooth is connected to said each tooth via said tooth origin for said each tooth;
   (e) finding a reference orthogonal curvilinear coordinate system for said each tooth; wherein said reference orthogonal curvilinear coordinate system comprises a reference origin for said tooth, a reference x-axis for said tooth, a reference y-axis for said tooth, and a reference z-axis for said tooth; wherein said reference origin for said tooth resides at a point on said reference virtual arch where an orthogonal projection from an orthogonal projection point meets said reference virtual arch; wherein said orthogonal projection point is located on said arbitrary plane where an orthogonal projection from said tooth origin of said tooth meets said arbitrary plane; wherein said reference x-axis for said tooth coincides with a tangent to said reference virtual arch at said reference origin; wherein said reference y-axis for said tooth is normal to said reference x-axis and passes through said reference origin; wherein said reference z-axis for said tooth is orthogonal to a plane formed by said reference x-axis for said tooth and said reference y-axis for said tooth and passes through said reference origin;
   (f) moving a tooth from said initial position to a desired position; and
   (g) measuring displacement for said tooth from said initial position to said desired position using said reference virtual arch, said reference orthogonal curvilinear coordinate system for said tooth, and said tooth axes system for said tooth.

2. The method of claim 1, wherein in step (c) said arbitrary plane is located such that sum of square of orthogonal distance of said each tooth origin from said arbitrary plane is minimized; and said reference virtual arch is shaped in said monotonous curve such that sum of square of orthogonal distance from said each orthogonal projection point to said reference virtual arch is also minimized.

3. The method of claim 1, wherein in step (c) said arbitrary plane is located such that sum of orthogonal distance of said each tooth origin from said arbitrary plane is minimized; and said reference virtual arch is shaped in said monotonous curve such that sum of orthogonal distance from each orthogonal projection point to said reference virtual arch is also minimized.

4. The method of claim 1, wherein said displacement of said tooth is mesiodistal displacement of said tooth; wherein said mesiodistal displacement is measured as length of bow segment along said reference virtual arch between said reference origin for said tooth and position of said tooth.

5. The method of claim 1, wherein said displacement of said tooth is buccolingual displacement of said tooth; wherein said buccolingual displacement is measured as orthogonal distance between a z-plane containing said reference z-axis for said tooth and a plane containing said tooth origin for said tooth and placed parallel to said z-plane.

6. The method of claim 1, wherein said displacement of said tooth is coronal-gingival displacement of said tooth; wherein said coronal-gingival displacement is measured as orthogonal distance between a y-plane containing said reference y-axis for said tooth and a plane containing said tooth origin for said tooth and placed parallel to said y-plane.

7. The method of claim 1, wherein said displacement of said tooth is a torque displacement of said tooth; wherein said torque displacement is measured as an angle $\alpha$ between said tooth z-axis and a tooth line; wherein said tooth line passes through said tooth origin; and wherein said tooth line is drawn parallel to said reference z-axis, when viewed from the perspective of the direction of said reference x-axis.

8. The method of claim 1, wherein said displacement of said tooth is an angulation displacement of said tooth; wherein said angulation displacement is measured as an angle $\beta$ between said tooth z-axis and a tooth line; wherein said tooth line passes through said tooth origin; and wherein said tooth line is drawn parallel to said reference z-axis, when viewed from the perspective of the direction of said reference y-axis.

9. The method of claim 1, further comprising the steps of:
(h) moving said tooth to another position;
(i) measuring displacement of said tooth while in said another position; and
(j) determining relative displacement of said tooth from said displacement of said tooth and said displacement of said tooth while in said another position.

10. The method of claim 1, wherein said displacement of said tooth is a rotation displacement of said tooth; wherein said rotation displacement is measured as an angle $\theta$ between said reference y-axis and said tooth y-axis when viewed from the perspective of the direction of said reference z-axis.

11. The method of claim 1, further comprising the steps of:
(h) moving said tooth to another position;
(i) measuring displacement of said tooth while in said another position;
(j) determining relative displacement of said tooth from said displacement of said tooth and said displacement of said tooth while in said another position; and
(k) repeating steps (h)-(j) until said relative displacement achieves a desired value.

12. The method of claim 1, wherein said jaw is lower jaw of said patient.

13. The method of claim 1, wherein said jaw is upper jaw of said patient.

* * * * *